(12) United States Patent
Cox et al.

(10) Patent No.: US 8,785,157 B2
(45) Date of Patent: Jul. 22, 2014

(54) METHOD FOR USING REF PROTEIN AS A TARGETED RECA-DEPENDENT NUCLEASE

(75) Inventors: Michael M. Cox, Oregon, WI (US); Marielle C. Eichhorn-Gruenig, Berlin (DE); James L. Keck, Monona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 304 days.

(21) Appl. No.: 13/208,985

(22) Filed: Aug. 12, 2011

(65) Prior Publication Data

US 2012/0088276 A1    Apr. 12, 2012

Related U.S. Application Data

(60) Provisional application No. 61/373,453, filed on Aug. 13, 2010.

(51) Int. Cl.
*C12N 15/113* (2010.01)

(52) U.S. Cl.
USPC ........ 435/91.53; 435/6.1; 435/91.1; 536/231; 536/23.2

(58) Field of Classification Search
USPC ............ 435/6, 91.1, 91.31, 183, 45, 5, 1, 6.1, 435/91.53; 514/1, 2, 44; 536/23.1, 24.5; 36/23.1, 23.2
See application file for complete search history.

(56) References Cited

U.S. PATENT DOCUMENTS 5,229,273 A   7/1993  Gottesman et al.
6,541,226 B1  4/2003  Shigemori et al.

OTHER PUBLICATIONS

Opalinska et al., Nature Rev., vol. 1, pp. 503-514 (2002).*
Lu et al., J. Bacteriology, vol. 171, No. 6, pp. 3427-3432 (1989).*
Shigemori et al, Nucleic Acids Research, vol. 32, No. 1, e4, pp. 1-8 (2004).*
Chen, et al., "Mechanism of homologous recombination from the RecA-ssDNA/dsDNA structures" (2008) Nature 453, pp. 489-494.
Cox, et al., "The bacterial RecA protein as a motor protein" (2003) Annu. Rev. Microbiol. 57, pp. 551-577.
Cox, et al., "Regulation of bacterial RecA protein function" (2007) Crit. Rev. Biochem. Mol. Biol. 42, pp. 41-63.
Gruenig, et al., "RecA-mediated SOS induction requires an extended filament conformation but no ATP hydrolysis" (2008) Mol. Microbiol. 69, pp. 1165-1179.
Jiang, et al., "The active form of DNA polymerase V is UmuD'(2)C-RecA-ATP" (2009) Nature 460, pp. 359-363.
Laufer, et al., "Enhancement of Escherichia coli plasmid and chromosomal recombination by the Ref function of bacteriophage P1" (1989) Genetics 123, pp. 465-476.
Lu, et al., "Stimulation of IS1 excision by bacteriophage P1 ref function" (1989) J. Bacteriol. 171, pp. 3427-3432.
Robu, et al., "Situational repair of replication forks: roles of RecG and RecA proteins" (2004) J. Biol. Chem. 279, pp. 10973-10981.
Scott "The zinc finger nuclease monopoly" (2005) Nature Biotechnology 23 (8), pp. 915-918.
Windle, et al., "A phage P1 function that stimulates homologous recombination of the Escherichia coli chromosome" (1986) Proc. Natl. Acad. Sci. U.S.A. 83, pp. 3885-3889.
Shigemori, et al., "Specific Cleavage of DNA Molecules at RecA-mediated triple-strand Structure" 2004 Nucleic Acids Research vol. 32, No. 1, p. E4.
Gruenig, et al., "Creating Directed Double-Strand Breaks with the Ref Protein: A Novel RecA-Dependent Nuclease From Bacteriophage P1" 2010 Journal of Biological Chemistry vol. 286, No. 10, pp. 8240-8251.
International Search Report mailed Apr. 11, 2011 for PCT/US2011/047584.

* cited by examiner

Primary Examiner — Jane Zara
(74) Attorney, Agent, or Firm — Quarles & Brady, LLP

(57) ABSTRACT

Kits and a method for cleaving double-stranded DNA using Ref and RecA protein and variants thereof at a site having a DNA sequence homologous to the sequence on a single-stranded DNA targeting fragment are disclosed.

10 Claims, 18 Drawing Sheets

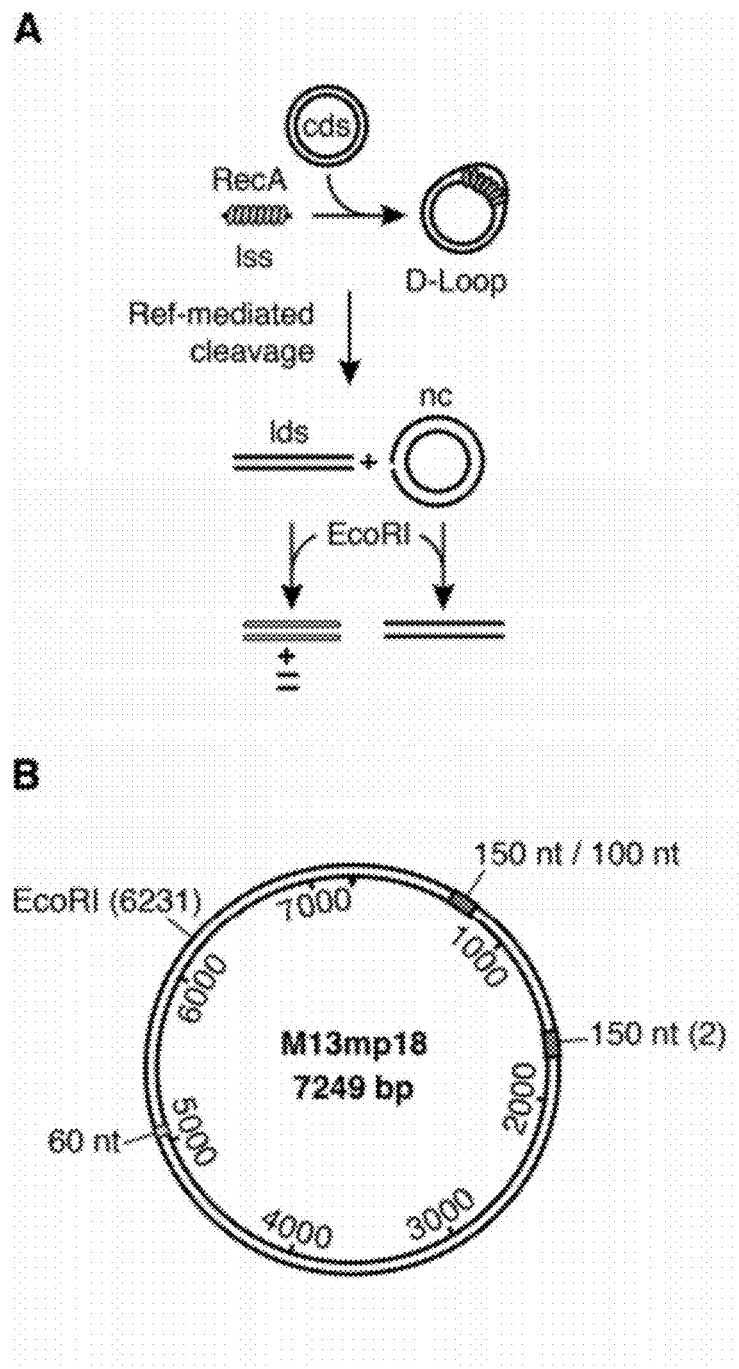
Figure 14A-B

METHOD FOR USING REF PROTEIN AS A TARGETED RECA-DEPENDENT NUCLEASE

CROSS-REFERENCE TO RELATED APPLICATIONS

This application claims the benefit of U.S. provisional Application No. 61/373,453, filed on Aug. 13, 2010, which is incorporated by reference herein in its entirety.

STATEMENT REGARDING FEDERALLY SPONSORED RESEARCH OR DEVELOPMENT

This invention was made with government support under GM032335 awarded by the National Institutes of Health. The government has certain rights in the invention.

BACKGROUND

A variety of endonucleases, designated "restriction enzymes" or "restriction endonucleases," are used in the art to cleave double-stranded DNA. These enzymes bind to specific sequences of DNA (the "recognition site") and cleave the DNA either at the recognition site or at a site that is some distance away from the recognition site.

Although restriction enzymes are an important and widely-used tool in molecular biology applications, the use of restriction enzymes has certain limitations resulting from the functional properties of the restriction enzymes. First, the locations at which restriction enzymes can cleave a given double-stranded DNA molecule are limited to the specific nucleotide sequences on the DNA molecule that correspond to the recognition sites of available restriction enzymes. A given restriction enzyme will cleave DNA only at or a certain distance from a specific DNA sequence corresponding to the restriction enzyme recognition site. Although different restriction enzymes may have different recognition sites, there are a limited number of available restriction enzymes, and thus a limited number of recognition sites at which double-stranded DNA can be cleaved. If cleavage is desired at a certain pre-determined location on the DNA molecule that does not contain a known restriction enzyme recognition site, such a site must be engineered into the DNA molecule, which can be a difficult and time-consuming task.

Second, restriction enzymes often cleave double-stranded DNA at more than one location, even if cleavage is desired at only a single location. Because restriction enzyme recognition sites generally have relatively short nucleotide sequences (e.g. 4-9 nucleotides), a double-stranded DNA molecule may frequently contain a given recognition site at multiple locations. In such a case, the use of restriction enzymes to cleave a double-stranded DNA molecule at a target location may result in cleavage at both the target location and at additional recognition sites where cleavage is not desired.

Zinc finger endonucleases (ZFN) have been used in gene therapy applications to introduce double strand breaks at a specific chromosomal locus and to induce homology-directed repair with an exogenously added donor DNA sequence (Scott, 2005). However, the use of this technology is limited by the need to generate a new ZFN for each specific knockdown target, which is a difficult and expensive task.

Thus, there is a need in the art for a method of cleaving a double-stranded DNA molecule at a pre-determined location in a sequence-directed manner, without requiring either the generation of a novel ZFN or the engineering of a restriction enzyme recognition site at the pre-determined location.

BRIEF SUMMARY OF THE INVENTION

By catalyzing recombinational DNA repair and by inducing the SOS response to DNA damage, the bacterial recombinase RecA plays a central role in maintenance of genome stability (Cox, 2003; Lusetti and Cox, 2002). To carry out these functions, RecA forms an activated nucleoprotein filament on single-stranded DNA (ssDNA) in the presence of an adenosine nucleotide cofactor (Yu and Egelman, 1992). A RecA filament bound to an oligonucleotide can invade and pair with a homologous duplex DNA, resulting in a displacement loop (D-loop). Besides functioning in recombination, RecA filaments also affect the activities of other proteins via direct interactions either by facilitating their autocatalytic cleavage or, in one case, by activating DNA polymerase V (Jiang et al., 2009). Additional proteins regulate almost every aspect of RecA function (Cox, 2007). About a dozen known proteins interact with RecA and intertwine its function with many aspects of DNA metabolism.

A search for new modes of RecA regulation led us to a recombination enhancement function gene, ref, encoded by bacteriophage P1. The Ref protein product of this gene increases chromosomal recombination, plasmid recombination, and the excision of an IS1 element in *E. coli*, all in a RecA-dependent fashion (Windle and Hays, 1986; Lu et al., 1989; Laufer et al., 1989).

We have surprisingly determined and disclose herein that Ref, in combination with RecA and a single-stranded DNA targeting oligonucleotide having a nucleotide sequence identical to a desired target sequence on a double-stranded DNA molecule, can be used to cleave the double-stranded DNA molecule at the desired target sequence. Specifically, RecA will bind to the single-stranded DNA targeting fragment to create a nucleoprotein complex. When this complex encounters a homologous double-stranded DNA molecule, the RecA will invade the double-stranded DNA molecule and pair the single-stranded DNA targeting fragment to the complementary sequence in one strand of the double-stranded DNA molecule. The other strand of the duplex (the one identical in sequence to the targeting oligonucleotide) is displaced, and a structure is formed that is often referred to as a D-loop. In the presence of the RecA-bound and paired DNA targeting fragment, Ref will cleave both strands of the targeted double-stranded DNA molecule at the desired target sequence, within the D-loop. Thus, the RecA, Ref, and single-stranded DNA targeting oligonucleotide act together as a designer nuclease, capable of cleaving any desired target sequence in a double-stranded DNA molecule. All that is required is to synthesize an oligonucleotide that is identical in sequence to the desired target. Accordingly, the present invention relates generally to methods and kits for nucleotide sequence-targeted cleavage of a double-stranded DNA molecule.

In a first aspect, the invention encompasses a method for cleaving a duplex DNA molecule at a chosen target nucleotide sequence. The method includes the step of assembling a complex of a single-stranded DNA targeting fragment with a RecA protein, a RecA protein homolog, or a polypeptide having substantial sequence identity to a RecA protein. RecA protein homologs that can be used in the method include without limitation a RecA protein homolog comprising the amino acid sequence of SEQ ID NO:21, SEQ ID NO:22, or SEQ ID NO:23. Preferably, a RecA protein is used to assemble the complex; more preferably, the RecA protein used to assemble the complex is the RecA protein comprising the amino acid sequence of SEQ ID NO:1 or the RecA protein comprising the amino acid sequence of SEQ ID NO:1 wherein lysine is substituted for glutamic acid at amino acid residue 38.

The single-stranded DNA targeting fragment includes a nucleotide sequence homologous to a target nucleotide sequence of a duplex DNA molecule. Preferably, the single-stranded DNA targeting fragment is from 30-1,000 nucleotides in length; more preferably, the single-stranded DNA targeting fragment is from 60-1,000 or 90-1,000 nucleotides in length. In the Examples reported below, the single-stranded DNA targeting fragment is from 60-150 nucleotides in length The method further includes the step of contacting the assembled complex with the duplex DNA molecule. When the assembled complex is contacted with the duplex DNA molecule, it forms a structure wherein the single-stranded DNA targeting fragment is paired with its complementary sequence on one strand of the duplex DNA, and wherein the other strand of the duplex DNA (the strand containing a sequence identical to a sequence on the single-stranded DNA targeting fragment) is displaced. In certain embodiments, this structure is known as a D-loop.

The method further includes the step of contacting a Ref protein, a Ref protein homolog, or a polypeptide having substantial sequence identity to a Ref protein with the duplex DNA molecule. As a result of the contact with the Ref protein, homolog, or variant, both strands of the targeted duplex DNA molecule are cleaved within the sequences defined by homology to the single-stranded DNA used as the targeting fragment.

Ref protein homologs that may be used in this step include without limitation polypeptides having one of the amino acid sequences of SEQ ID NO:3, SEQ ID NO:4, SEQ ID NO:5, and SEQ ID NO:6. Preferably, the Ref protein, Ref protein homolog, or polypeptide having a substantial sequence identity to a Ref protein that is used in this step has a ββα-metal core fold motif having the amino acid sequence of amino acid residues 112-123 of SEQ ID NO:2, and further contains two metal binding motifs, one such motif C-terminal to the ββα-metal core fold motif and having the amino acid sequence of amino acid residues 96-99 of SEQ ID NO:2, and one such motif N-terminal to the ββα-metal core fold motif and having the amino acid sequence of amino acid residues 130-133 of SEQ ID NO:2. More preferably, the Ref protein used in this step is a Ref protein comprising the amino acid sequence of SEQ ID NO:2.

Although the complex must be formed before the duplex DNA molecule can be displaced and cleaved by Ref, the order in which the components listed in the steps are added is not critical to the method. Thus, the method is effective if the steps are carried out in sequential manner, or alternatively, if the components for two or more of the steps are added at the same time.

In certain embodiments, one or more of the steps described above occur within a solution containing a divalent metal ion. Preferably, the divalent metal ion is $Mg^{2+}$ or $Mn^{2+}$; more preferably, the divalent metal ion is $Mg^{2+}$.

In a second aspect, the invention encompasses a kit for cleaving a duplex DNA molecule at a chosen target nucleotide sequence. The kit includes a first composition containing a purified RecA protein, a purified RecA protein homolog, or a purified polypeptide having substantial sequence identity to a RecA protein. Purified RecA protein homologs that can be used in the first composition include without limitation a RecA protein homolog comprising the amino acid sequence of SEQ ID NO:21, SEQ ID NO:22, or SEQ ID NO:23. Preferably, the first composition contains a purified RecA protein; more preferably, the RecA protein has the amino acid sequence of SEQ ID NO:1 or the amino acid sequence of SEQ ID NO:1 wherein lysine is substituted for glutamic acid at amino acid residue 38.

The kit also includes a second composition containing a purified Ref protein, a purified Ref protein homolog, or a purified polypeptide having substantial sequence identity to a Ref protein. In certain embodiments, the second composition contains a purified Ref protein homolog having one of the amino acid sequences selected from the group consisting of SEQ ID NO:3, SEQ ID NO:4, SEQ ID NO:5, and SEQ ID NO:6. Preferably, the purified Ref protein, purified Ref protein homolog, or purified polypeptide having a substantial sequence identity to a Ref protein that is used in the second composition contains a ββα-metal core fold motif having the amino acid sequence of amino acid residues 112-123 of SEQ ID NO:2, and further contains two metal binding motifs, one such motif C-terminal to the ββα-metal core fold motif and comprising the amino acid sequence of amino acid residues 96-99 of SEQ ID NO:2, and one such motif N-terminal to the ββα-metal core fold motif and comprising the amino acid sequence of amino acid residues 130-133 of SEQ ID NO:2. More preferably, the second composition contains a purified Ref protein having the amino acid sequence of SEQ ID NO:2.

The kit may further include a third composition containing a customized single-stranded DNA targeting fragment. The targeting fragment may include a nucleotide sequence homologous to a target nucleotide sequence of a duplex DNA molecule. Preferably, the customized single-stranded DNA targeting fragment is from 30 to 1,0000 nucleotides in length.

In some embodiments, the first composition, the second composition, or both may additionally contain a suitable buffer solution, a divalent metal ion (preferably, $Mn^{2+}$ or $Mg^{2+}$; more preferably, $Mg^{2+}$), and/or ATP or dATP.

These and other features of the present invention will become apparent to the skilled artisan from the following detailed description considered in conjunction with the accompanying drawings.

BRIEF DESCRIPTION OF DRAWINGS

FIG. 5A shows an SDS-PAGE analysis of selected fractions from a Sephacryl S200 gel filtration column. The last lane contains purified Ref that was not run over the column. FIG. 5B shows a nuclease assay of the same fractions used in FIG. 5A, carried out as described in Example 1. An equal volume of each of the fractions from the gel filtration column was added to the reactions in order to track activity.

FIG. 10A is a sequence alignment of several recognized Ref protein homologs. Ref P1 is SEQ ID NO:2. The homologs shown are from bacteriophages P7 (SEQ ID NO:4) and phi-W39 (SEQ ID NO:3), and from the bacteria *S. enterica* subsp. *Enterica serovar* Newport strain SL317 (SEQ ID NO:5) and *B. avium* (SEQ ID NO:6). Alignments were carried out with the program ClustalW. Invariant (*) and conserved (: or .) residues are marked. Sequences of importance are underlined. Elements of secondary structure are noted in the diagram above the P1 Ref sequence, with open bars representing α-helical segments and open arrows representing β conformation. FIG. 10B is a drawing of the overall structure of the Ref protein. FIG. 10C is a sample of electron density showing amino acid side chains in the putative Ref active site presented in stereo.

FIG. 11 shows that Ref protein remains intact after crystallization.

FIG. 13B shows superposition of DNA from the E9 DNase/DNA co-crystal structure (PDB ID 1V14) onto Ref. This model was produced by superimposing the ββα folds of the two proteins.

FIG. 14A is a schematic diagram showing the reaction scheme used in Example 1. RecA (0.67 µM) was incubated with oligonucleotide (4 µMnt) for 20 min with 3 mM ATP to allow RecA filament formation. Circular dsDNA (8 µMnt) was added, and D-loop formation occurred. After 20 min, Ref (48 nM) was added to the reactions followed by a 180-min incubation producing linear dsDNA and leaving some uncleaved dsDNA. The reactions were stopped, and the DNA was digested using EcoRI. This produced cleavage products of expected size when the DNA had been linearized by Ref. lds, linear dsDNA; lss, linear ssDNA; cds, supercoiled dsDNA. FIG. 14B is a map of M13mp18 circular dsDNA showing locations of oligonucleotides and restriction site. FIG. 14 shows that RecA-mediated D-loop formation results in directed dsDNA cleavage by Ref.

FIG. 15 shows that Ref cleaves DNA at multiple sites within the D-loop.

Figure 1:
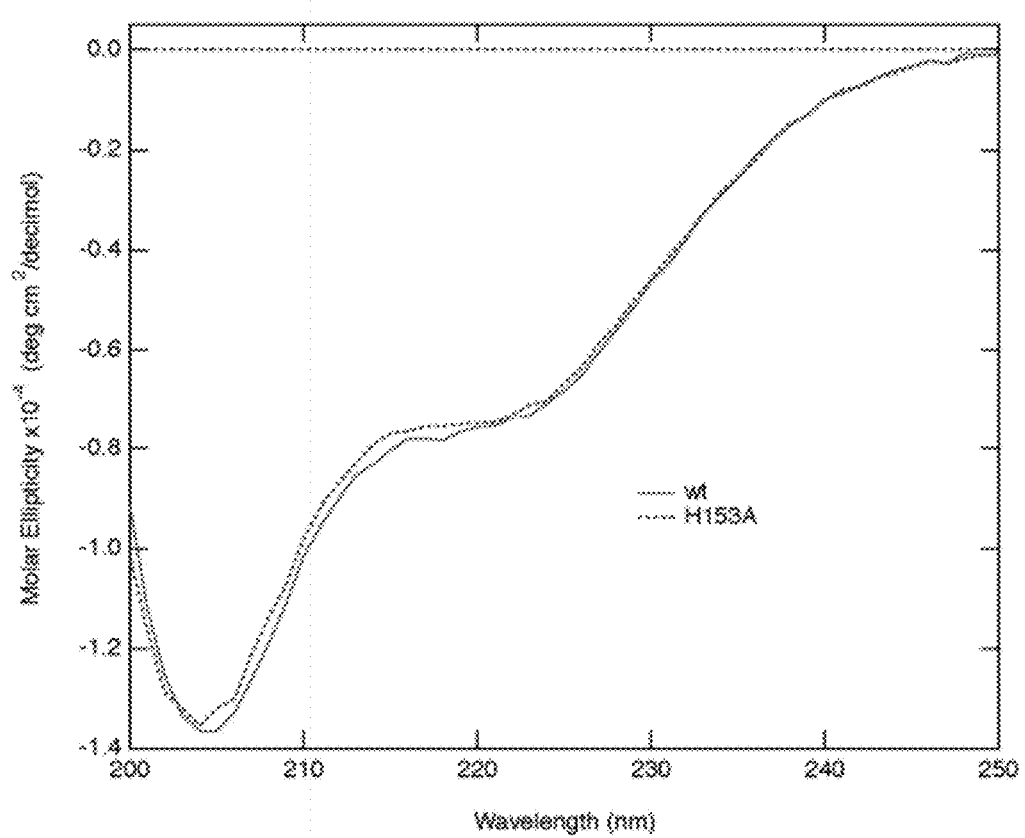
FIG. 1 shows a graph of molar ellipticity vs. wavelength obtained using dichroism spectroscopy for wild-type Ref (solid line) and Ref H153A (dashed line). The circular dichroic spectra show that Ref H153A is folded similarly to wild-type Ref.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

We have developed a method and kits for cleaving a double-stranded (duplex) DNA molecule at a homologous target sequence, where homologous is defined as a site with one strand identical and the other complementary to the sequence of a single-stranded DNA targeting fragment. In addition to the targeted duplex DNA molecule and the single-stranded DNA targeting fragment, the method requires both a RecA protein, homolog or variant, and a Ref protein, homolog or variant. The method is preferably performed in the presence of ATP and a divalent cation, such as $Mg^{2+}$ or $Mn^{2+}$.

In a first aspect, the invention encompasses a method of cleaving a duplex DNA molecule at a target nucleotide sequence. The duplex DNA molecule that is cleaved is limited only in that it is a double-stranded DNA molecule, meaning that is contains two DNA strands that have complementary nucleotide sequences, with each strand aligned in an antiparallel direction relative to the other strand (3'-5' versus 5'-3'). "Duplex DNA" encompasses all such molecules, including without limitation genomic, non-genomic, synthetic, or semi-synthetic double-stranded DNA molecules or fragments thereof. Non-limiting examples of duplex DNA include prokaryotic and eukaryotic chromosomes, plasmids and plasmid vectors, double-stranded viral DNA, double-stranded mitochondrial DNA, double-stranded synthetic oligonucleotides, and fragments thereof. The duplex DNA that is cleaved using the method is not limited by the surrounding environment or by any associated structures. Accordingly, the method can be used in any environment, including without limitation in an in vitro, in situ, in vivo, or ex vivo environment. The duplex DNA may be associated with one or more DNA-binding proteins, including histones and other proteins that are known to facilitate the formation of DNA-protein complexes.

The method includes the step of assembling a complex between (a) a single-stranded DNA targeting fragment comprising a nucleotide sequence that is homologous to a target nucleotide sequence of a duplex DNA molecule and (b) a RecA protein, a RecA protein homolog, or a polypeptide having substantial sequence identity to a RecA protein. This step may be performed in any setting known in the art, including without limitation an in vitro, ex vivo, in vivo, or in situ setting.

By "single-stranded DNA targeting fragment" we mean a single-stranded segment of DNA designed to share homology, preferably of at least 30 nucleotides, with a duplex DNA molecule sequence of interest. Since the RecA-promoted D-loop formation reaction is highly dependent on sequence identity, we anticipate that no more than two nucleotide mismatches can be tolerated within a 30 nucleotide DNA target. The sequence of interest is at the location where the duplex DNA molecule is to be cleaved. The actual cleavage site include sequences near the 3' end of the targeting DNA segment. Preferably, the targeting fragment is 30-1,000 nucleotide long; more preferably, it is 60-1,000 or 90-1,000 nucleotides long. In the Examples below, we have illustrated the method using targeting fragments of from 60-150 nucleotides long.

The DNA targeting fragment may be initially double-stranded and rendered single-stranded using a variety of techniques, including without limitation (a) heat denaturation, (b) asymmetric PCR, or (c) specific degradation of the complementary strand by nucleases using a procedure that blocks the degradation of the desired strand, or by the combined activity of a nuclease/helicase combination. Alternatively, the targeting fragment may be created as a single-stranded molecule. Methods of synthesizing small single-stranded oligonucleotides are well-known in the art, and oligonucleotides having a specified sequence can also be custom ordered from a variety of commercial sources. Optionally, the DNA targeting fragment is previously purified.

It is preferred that the RecA protein used in the method is either *E. coli* (strain K12) RecA protein (Uniprot sp P0A7G6) having the amino acid sequence of SEQ ID NO:1, or the mutated RecA protein having the amino acid sequence of SEQ ID NO:1, except that lysine is substituted for glutamic acid at amino acid residue 38 (RecAE38K).

Homologs of *E. coli* RecA protein can also be used in the method. By homolog, we mean a protein putatively derived from a common ancestor that performs the same function as RecA in other bacterial species or related families. Non-limiting examples of RecA homologs known in the art include the RecA proteins from *Deinococcus radiodurans*, having the amino acid sequence of SEQ ID NO:21 (NCBI Accession No. BAA21330; Version BAA21330.1), and the RecA protein from *Pseudomonas aeruginosa*, having the amino acid sequence of SEQ ID NO:22 (NCBI Accession No. ACT64220; Version ACT64220.1). Another example, the RecA protein derived from *Neisseria gonorrhoeae*, having the amino acid sequence of SEQ ID NO:23 (NCBI Accession No. AAB49193; Version AAB49193.1), is fully functional as a co-nuclease for Ref protein. The method also includes the use of polypeptide variants having substantial sequence identity to the *E. coli* RecA of SEQ ID NO:1. By "substantial sequence identity," we mean that the polypeptide has at least 40% sequence identity to SEQ ID NO:1 and retains the RecA functionality. Preferably, the sequence identity with the reference sequence is at least 90%; more preferably, it is at least 98%. We envision that other RecA mutants in addition to RecAE38K that are more effective than the wild type RecA protein can be created and can substitute for the RecA protein in the method described herein. Procedures for creating and screening such mutants are well known in the art. Preferably, the RecA protein, RecA homolog, or RecA variant used in the method is previously purified.

The method further includes the step of assembling a complex of RecA protein, the RecA protein homolog, or the polypeptide having substantial sequence identity to a RecA protein with the single-stranded targeting segment, that is in turn used in the previously described step to pair with duplex (double-stranded) DNA molecule. Formation of this complex further requires the presence of $Mg^{2+}$ or $Mn^{2+}$ ion, and ATP or an ATP analog. This step may be performed in any setting known in the art, including without limitation an in vitro, ex vivo, or in vivo or in situ setting. The duplex DNA molecule has a target nucleotide sequence that is homologous to a nucleotide sequence of the DNA targeting fragment at the location where DNA duplex molecule is to be cleaved, but is not otherwise limited. The DNA duplex molecule may be linear or circular, and may be genomic or non-genomic. The DNA molecule may be of viral, prokaryotic, eukaryotic, or synthetic origin, and optionally may be purified before being used in the method.

The method additionally includes the step of contacting a Ref protein, a Ref protein homolog, or a polypeptide having substantial sequence identity to a Ref protein with the duplex DNA molecule described above. This step may be performed in any setting known in the art, including without limitation an in vitro, ex vivo, or in vivo or in situ setting.

It is preferred that the Ref protein used in the method is the *Enterobacteria* phage P1 Ref protein (Uniprot sp 35926) having the amino acid sequence of SEQ ID NO:2. Homologs of Ref protein can also be used in the method. By homolog, we mean a protein putatively derived from a common bacteriophage ancestor that performs the same function as Ref in other bacteriophage or bacterial species. Non-limiting examples of Ref homologs known in the art include the *Enterobacteria* phage φW39 recombination enhancement function (Ref) protein having the amino acid sequence of SEQ ID NO:3 (NCBI Accession No. AAV84933; Version AAV84933.1); the *Enterobacteria* phage P7 Ref protein having the amino acid sequence of SEQ ID NO:4 (NCBI Accession No. AAQ07480; Version AAQ07480.1); the recombination enhancement function (Ref) protein of *Salmonella enterica* subsp. *Enterica serovar* Newport str. SL317 having the amino acid sequence of SEQ ID NO:5 (NCBI Accession No. EDX48505; Version EDX48505.1); and the putative phage recombination protein of *Bordetella avium* str. 197N having the amino acid sequence of SEQ ID NO:6 (Uniprot tr Q2L2X9).

The method also includes the use of polypeptide variants having substantial sequence identity to the phage P1 Ref of SEQ ID NO:2. By "substantial sequence identity," we mean that the polypeptide has at least 75% sequence identity to SEQ ID NO:2 and retains the Ref functionality. Preferably, the sequence identity with the reference sequence is at least 90%; more preferably, it is at least 98%. We envision that other Ref mutants that are more effective than the wild type Ref protein can be created and can substitute for the Ref protein in the method described herein. Procedures for creating and screening such mutants are well known in the art. Preferably, the Ref protein, Ref homolog, or Ref variant used in the method is previously purified.

We have determined that the active Ref protein used in the Examples below includes a ββα-metal core fold motif having the amino acid sequence of amino acid residues 112-123 of SEQ ID NO:2, and further includes two metal binding motifs, one such motif C-terminal to the ββα-metal core fold motif and having the amino acid sequence of amino acid residues 96-99 of SEQ ID NO:2, and the other such motif N-terminal to the ββα-metal core fold motif and having the amino acid sequence of amino acid residues 130-133 of SEQ ID NO:2. Accordingly, in some embodiments, the Ref protein, homolog, or variant used in the method contains these motifs.

When the steps are performed as described, the duplex DNA molecule is cleaved at the target nucleotide sequence. Although it is preferred that the above-described steps are performed in the order presented above, performing the steps in this order is not essential to the cleavage of that duplex DNA molecule. Thus, the described steps may be performed in any order. Furthermore, the step using the RecA protein, homolog or variant, and the step using a Ref protein, homolog or variant may be performed at the same time. In such embodiments, a fusion protein encompassing both the RecA protein, homolog or variant, and the Ref protein, homolog or variant may be used in the method.

Successful cleavage of the duplex DNA molecule further requires the presence of ATP and a divalent metal ion. Preferably, the divalent metal ion is $Mg^{2+}$ or $Mn^{2+}$; more preferably, the divalent metal ion is $Mg^{2+}$. Accordingly, one or more of the steps described above may be performed in the presence of ATP and/or a divalent metal ion. The divalent metal ion is preferably $Mg^{2+}$ or $Mn^{2+}$ and is more preferably $Mg^{2+}$.

Preferably, one or more of the steps is performed in a suitable buffer. A preferred buffer has a pH of 6.5 to 8.5 and magnesium ion concentration of 3-12 mM and may contain ATP or dATP and an ATP regeneration system (e.g., Phosphoenolpyruvate and pyruvate kinase, or creatine phosphate and creatine kinase). Recipes for preferred buffers are described, for example, in Gruenig et al., 2008.

In a second aspect, the invention encompasses a kit for cleaving a duplex DNA molecule at a target nucleotide sequence. The kit includes a first composition including a purified RecA protein, a purified RecA protein homolog, or a purified polypeptide having substantial sequence identity to a RecA protein. Purified RecA protein homologs that can be used in the first composition include without limitation a RecA protein homolog comprising the amino acid sequence of SEQ ID NO:21, SEQ ID NO:22, or SEQ ID NO:23. The first composition may include a suitable buffer solution containing the purified RecA protein, homolog, or variant, and optionally contains a divalent cation, preferably $Mg^{2+}$ or $Mn^{2+}$, and/or ATP. A preferred buffer has a pH of 6.5 to 8.5 and magnesium ion concentration of 3-20 mM, and may further contain ATP or an ATP regeneration system (e.g., Phosphoenolpyruvate and pyruvate kinase, or creatine phosphate and creatine kinase). Recipes for preferred buffers are described, for example, in Gruenig et al., 2008.

It is preferred that the purified RecA protein contained in the first composition is either *E. coli* (strain K12) RecA protein (Uniprot sp POA7G6) having the amino acid sequence of SEQ ID NO:1, or the mutated RecA protein having the amino acid sequence of SEQ ID NO:1, except that lysine is substituted for glutamic acid at amino acid residue 38 (RecAE38K). Alternatively, purified homologs of *E. coli* RecA protein or purified polypeptide variants having substantial sequence identity to the *E. coli* RecA of SEQ ID NO:1 can be used in the first composition.

The kit additionally includes a second composition containing a purified Ref protein, a purified Ref protein homolog, or a purified polypeptide having substantial sequence identity to a Ref protein. Alternatively, the first composition may comprise a purified fusion protein encompassing both the RecA protein, homolog or variant, and the Ref protein, homolog or variant. The first composition may include a suitable buffer solution containing the purified Ref protein, homolog, or variant. A preferred buffer has a pH of 6.5 to 8.5. Recipes for preferred buffers are described, for example, in Gruenig et al., 2008.

The purified Ref protein contained in the second composition is preferably the Enterobacteria phage P1 Ref protein (Uniprot sp 35926) having the amino acid sequence of SEQ ID NO:2. Alternatively, purified homologs of Ref protein or purified polypeptide variants having substantial sequence identity to the phage P1 Ref of SEQ ID NO:2 can be used in the second composition.

In certain embodiments, the purified Ref protein, homolog, or variant used in the second composition contains the ββα-metal core fold motif and the two metal binding motifs described above.

In preferred embodiments, the kit contains a third composition containing a customized single-stranded DNA targeting fragment. Preferably, the customized single-stranded DNA targeting fragment is from 30 to 1,000 nucleotides in length; more preferably, the targeting fragment is from 90 to 1,000 nucleotides in length. In the Examples below, we have demonstrated the use of DNA targeting fragments of 60 and 150 nucleotides in length. Preferably, the customized single-stranded DNA targeting fragment is purified, and the third composition may optionally contain a stabilizing buffer.

The methods and kits disclosed herein will facilitate the cleavage of double-stranded DNA in a directed manner not provided by any other technique currently known in the art. As a research tool, the methods and kits can be used for directed ex vivo DNA cleavage, and could also be used to create eukaryotic or bacterial cell gene knockouts or transgenic organisms for use in research.

The methods and kits may also be used therapeutically. For example, the methods and kits could be used to digest HIV gene sequences embedded in a human genome. Because the disclosed Ref/RecA endonuclease system and associated method can be targeted to any genomic sequence by using a specific single-stranded DNA targeting fragment homologous to a targeted genome sequence, any specific genome sequence can be targeted for inactivation or removal using the same Ref/RecA system/method.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Demonstration of Targeted Co-Nuclease Function for Reca Recombinase with the Bacteriophage P1 Ref Protein A. Summary A universal restriction enzyme that could promote specific DNA cleavage at any desired DNA sequence would find a wide array of applications in biotechnology, but no precedent for such an enzyme exists. In this example, we demonstrate that the bacteriophage P1-encoded Ref protein functions as a RecA-dependent nuclease. RecA protein filaments are used to activate a latent nuclease function in Ref. With single-stranded DNA substrates, RecA filament-activated Ref catalyzes large-scale DNA degradation. In long duplex DNA, Ref nuclease activity can be localized to RecA-containing D-loops.

The crystal structure of Ref provides evidence that Ref is a member of a new sub-class of HNH-family nucleases. The core nuclease fold lacks apparent DNA-binding elements found in other HNH enzymes and suggests that interaction between RecA and Ref facilitates Ref activation. Using the RecA/Ref system, any duplex DNA sequence can be targeted for cleavage in an oligonucleotide-directed fashion, making the disclosed combination a remarkably adaptable molecular biological tool.

B. Experimental Procedures

Proteins. The native *E. coli* wild type RecA and single stranded DNA binding proteins were purified as described previously (Petrova et al., 2009). The concentration of the purified RecA and single-stranded DNA binding proteins was determined from the absorbance at 280 nm using the extinction coefficients of $2.23 \times 10^4$ $M^{-1}$ $cm^{-1}$ (Craig et al., 1981) and $2.83 \times 10^4$ $M^{-1}$ $cm^{-1}$, respectively (Lohman and Overman, 1985). The non-cleavable UmuD1 protein (Koch et al., 1992) was a generous gift from M. Goodman. LexA S119A (Slilaty and Little, 1987) was a generous gift from J. Little. Wild type LexA was purified as described (Gruenig et al., 2008). DinI was purified as described (Lusetti et al., 2004).

The RecA E38K mutant was purified like wild type RecA with the following modifications. The polyethyleneimine pellet containing RecA E38K was washed with R buffer (20 mM Tris Cl (80% cation; pH 7.5) 0.1 mM EDTA 1 mM DTT 10% glycerol), not R plus 150 mM $(NH_4)_2SO_4$. The protein was then purified by successive chromatographic steps using a butyl-Sepharose column, an SP-Sepharose column, a ceramic hydroxyapatite column, and a Sephacryl S-300 gel filtration column. RecA E38K K72R and RecA K72R were purified as described previously (Gruenig et al., 2008). The concentrations of all three RecA mutant proteins were determined from the absorbance at 280 nm using the extinction coefficient $2.23 \times 10^4$ $M^{-1}$, $cm^{-1}$, and they are stored in R buffer.

DNA Substrates. The circular ssDNA from bacteriophage M13mp18 (7249 nucleotides) was prepared essentially as described (Messing, 1983; Neuendorf and Cox, 1986). The linear single-stranded DNA was prepared by annealing an oligonucleotide complementary to the BamHI site followed by a BamHI restriction digest. The linear ssDNA was cleaned up by removal of the oligonucleotide using a YM-100 Centricon. The concentration of circular and linear ssDNA was determined by absorbance at 260 nm using $36\ \mu g\ ml^{-1}\ A_{260}^{-1}$ as the conversion factor. The M13mp18 circular dsDNA was prepared as described in Messing, 1983; Neuendorf and Cox, 1986; and Haruta et al., 2003. The M13 mp18 linear dsDNA substrate was prepared by digesting M13mp18 circular dsDNA with PstI. All DNA concentrations are given in total nucleotides. Oligonucleotides were purchased from Integrated DNA Technologies. Sequences of oligonucleotides used in this study are presented in Table 1.

TABLE 1

Primers and oligonucleotides used

| Name | Length (nt) | Sequence | Complementary to M13mp18 at bases |
|---|---|---|---|
| rlb1 | 150 | TTTTGGTTTTTATCGTCGTCTGGTAAACGAG GGTTATGATAGTGTTGCTCTTACTATGCCTC GTAATTCCTTTTGGCGTTATGTATCTGCATT AGTTGAATGTGGTATTCCTAAATCTCAACTG | 597-746 |

TABLE 1-continued

Primers and oligonucleotides used

| Name | Length (nt) | Sequence | Complementary to M13mp18 at bases |
|---|---|---|---|
| | | ATGAATCTTTCTACCTGTAATAATGT (SEQ ID NO: 7) | |
| msc1 | 60 | ATTCTTACGCTTTCAGGTCAGAAGGGTTCTA TCTCTGTTGGCCAGAATGTCCCTTTTATT (SEQ ID NO: 8) | 5041-5100 |
| den7 | 50 | GGCCTCGCGGTAGCTGAGCTCGGAGCGCAC GATTCGCACTGCTGATGTTC/36-FAM (SEQ ID NO: 9) | N/A |
| galK | 150 | GCATTTGGCTACCCTGCCACTCACACCATTC AGGCGCCTGGCCGCGTGAATTTGATTGGTG AACACACCGACTACAACGACGGTTTCGTTC TGCCCTGCGCGATTGATTATCAAACCGTGAT CAGTTGTGCACCACGCGATGACCGTAA (SEQ ID NO: 10) | N/A |
| mcg1 | | 56-FAM/TAACATCAGCAGTGCGAATCGTGCG CTCCGAGCTCAGCTACCGCGAGGCCTGCA (SEQ ID NO: 11) | N/A |
| den10 | 50 | GAACATCAGCAGTGCGAATCGTGCGCTCCG AGCTCAGCTACCGCGAGGCC (SEQ ID NO: 12) | N/A |
| mcg2 | 54 | GAACATCAGCAGTGCGAATCGTGCGCTCCG AGCTCAGCTACCGCGAGGCCTGCA (SEQ ID NO: 13) | N/A |
| mcg3 | 150 | TCCCGACTGGAAAGCGGGCAGTGAGCGCAA CGCAATTAATGTGAGTTAGCTCACTCATTAG GCACCCCAGGCTTTACACTTTATGCTTCCGG CTCGTATGTTGTGTGGAATTGTGAGCGGAT AACAATTTCACACAGGAAACAGCTATGA (SEQ ID NO: 14) | 6070-6219 |
| HJ1 | 41 | FAM*- 56CCCGTGATCACCAATGCAGATTGACGAAC CTTTGCCCACGT (FAM-56-SEQ ID NO: 15) | |
| HJ2 | 41 | GACGTGGGCAAAGGTTCGTCAATGGACTGA CAGCTGCATGG (SEQ ID NO: 16) | |
| HJ3 | 41 | GCCATGCAGCTGTCAGTCCATTGTCATGCTA GGCCTACTGC (SEQ ID NO: 17) | |
| HJ4 | 41 | GGCAGTAGGCCTAGCATGACAATCTGCATT GGTGATCACGG (SEQ ID NO: 18) | |
| ANP003 | 19 | GACGTGGGCAAAGGTTCGT (SEQ ID NO: 19) | |
| ANP004 | 18 | TCATGCTAGGCCTACTGC (SEQ ID NO: 20) | |

*FAM, 6-carboxyfluorescein

Cloning, Overexpression, and Purification of Ref and Ref Variants. The P1 ref gene was obtained by PCR amplification, cloned, and expressed using the vector pET21A (Novagen). The resulting plasmid was designated pEAW584. The presence of wt P1 ref was confirmed by direct sequencing.

Standard methods were used to alter the ref gene in plasmid pEAW584, changing the CAT bases at 457-459 (His) at amino acid 153 to GCT (Ala). The resulting plasmid was designated pEAW665. Ref ΔN76 was constructed beginning with pEAW584. A PCR primer was constructed to amplify codons 77-185 of the Ref gene in pEAW584, adding a new Met initiator codon on the altered N terminus. The upstream primer consisted of an NdeI site and bases 229-270 of the P1 ref gene. The ATG of the NdeI site codes for the Met. For better codon usage in E. coli, the GGG coding for Gly at amino acid (aa) 2 (codon 77) was changed to GGT, the AGA coding for Arg at aa 3 was changed to CGT, the ACA coding for Thr at aa 4 was changed to ACC, the ACG coding for Thr at aa 6 was changed to ACC, and the CGG coding for Arg at aa 10 was changed to CGT. The downstream primer was the same used to clone pEAW584. The PCR product was digested with NdeI and BamHI and ligated to pET21A (Novagen) digested with the same enzymes. The resulting plasmid was designated pEAW685. The structure of both mutant ref genes was confirmed by direct sequencing.

Competent cells of E. coli strain BL21(DE3) were transformed with plasmid pEAW584. Ten liters of culture were grown in LB broth to an $A_{600}$ of 0.51. Ref protein expression was induced by the addition of isopropyl 1-thio-β-D-galactopyranoside to 0.4 mM. After a 3-h 10-min outgrowth at 37°

C., 24.6 g of cells were harvested by centrifugation, flash-frozen in liquid $N_2$, and stored at −80° C. The protein expressed is the native, 186-amino acid polypeptide without tags.

All purification steps were carried out at 4° C. Purification entailed polyethyleneimine precipitation and pellet extraction, precipitation with $(NH_4)_2SO_4$, and chromatography successively using butyl-Sepharose, Source 15 Q, ceramic hydroxyapatite columns, and Sephacryl S-100 gel filtration columns. This was followed by another butyl-Sepharose chromatography step. The protein was concentrated using Amicon Centricon-Plus 20 and dialyzed against Ref storage buffer (R plus 200 mM potassium glutamate), flash-frozen in liquid $N_2$, and stored at 80° C. The protein was >99% pure and free of detectable nuclease activity when incubated at 37° C. for 2 h with different DNA substrates (circular ssDNA, linear and supercoiled dsDNA, and labeled oligonucleotides) in a buffer containing 25 mM Tris-OAc (80% cation, pH 7.6), 1 mM DTT, 3 mM potassium glutamate, 10 mM $Mg(OAc)_2$, and 5% (w/v) glycerol (buffer A).

The concentration of the Ref protein was determined from the absorbance at 280 nm using the extinction coefficient $2.851 \times 10^4$ $M^{-1}$ $cm^{-1}$. The Ref extinction coefficient ($\varepsilon_{nat,280\ nm} = 2.851 \times 10^4 \pm 0.108$ $M^{-1}$ $cm^{-1}$) was determined during the course of the present work using procedures described elsewhere (Marrione and Cox, 1995; Robu et al., 2004). The identity of the purified protein was confirmed by mass spectrometry. The measured mass of the protein was 21,326 Da, in very good agreement with the calculated mass of Ref protein of 21,329 Da (with the initiator Met residue still present). In the course of these studies, a higher molecular weight band on SDS-PAGE gels was observed that corresponded to the approximate size of a Ref dimer. The identity of this band was confirmed to be Ref by mass spectrometry.

The Ref H153A and ΔN76 mutant proteins were purified with procedures using very similar growth, induction, cell harvesting, and early fractionation steps. Ref 153A was purified with successive chromatographic steps employing butyl-Sepharose, ceramic hydroxyapatite, and Sephacryl S-100 followed by additional ceramic hydroxyapatite and butyl-Sepharose steps. The protein was >99% pure by SDS-PAGE and free of any detectable nuclease contamination. Ref H153A is folded the same as wild type Ref as confirmed by CD spectroscopy (FIG. 1). The Ref ΔN76 protein was purified with successive butyl-Sepharose, ceramic hydroxyapatite, Sephacryl S-100, and Source 15 Q-Sepharose. The protein was >99% pure and free of detectable nuclease activity. The concentration of the Ref ΔN76 protein was determined from the absorbance at 280 nm using a calculated extinction coefficient of 15,220 $M^{-1}$ $cm^{-1}$. The identity of the Ref ΔN76 protein was confirmed by excising the protein band from a gel and digesting with trypsin. The products were subjected to MALDI-TOF/TOF mass spectrometry (Applied Biosystems/MDS SCIEX 4800) for identification of peptides. Peptides detected and sequenced (many repeatedly) were all consistent with the predicted sequence of Ref ΔN76 and included 92% of the amino acid residues in the protein.

Electrophoretic Mobility Shift Assays. A single-stranded 50-mer oligonucleotide, 3'6-carboxyfluorescein-labeled den7, was purchased from Integrated DNA Technologies (Table 1). To generate labeled blunt-ended double-stranded DNA, the labeled 50-mer was annealed to an unlabeled complementary 50-mer, den10 (Table 1). The two labeled DNA substrates were used at 2.5 or 5 μM (in total nucleotides) for the ssDNA or dsDNA oligos, respectively. The DNA binding reactions also contained buffer A. The reactions (10 μl) containing the indicated concentrations of Ref protein (replaced in controls with Ref storage buffer) were incubated at 37° C. for 10 min. Then 5 μl of 6× loading buffer (18% (w/v) Ficoll, 20 mM Tris-OAc 80% cation) was added to 10 μA of thereactions, and the reactions were loaded onto a native 8% polyacrylamide gel and subjected to electrophoresis in TBE buffer (90 mM Tris borate and 10 mM EDTA). The longer M13 mp18 circular ssDNA or linear dsDNA substrates were used at a concentration of 10 μMnt$^3$ in reactions (40 μl) containing otherwise the same components as described above. The abbreviations used are: nt, nucleotide(s); ATPγS, adenosine 5'-β-(thiotriphosphate). Various concentrations of Ref were added to the reactions and incubated for 40 min at 37° C. Then 5 μl of 6× loading buffer (18% (w/v) Ficoll, 20 mM Tris-OAc 80% cation) was added to the reactions, and the entire reactions were loaded onto a native 0.5% agarose gel and subjected to electrophoresis in TE buffer (10 mM Tris acetate (80% cation) and 1 mM EDTA).

Nuclease Assay. The reactions were carried out at 37° C. and contained buffer A, an ATP regeneration system (10 units/ml pyruvate kinase and 3.5 mM phosphoenolpyruvate), and 4 μMnt M13 mp18 circular ssDNA. The aforementioned components were incubated with 2.4 μM RecA for 10 min. Three mM ATP was added followed by a 15-min incubation to allow for RecA filament formation before Ref was added at the concentrations indicated. After 20 min, 20 μA of the reaction was stopped by incubation with 5 μl of 20 mg/ml Proteinase K for 60 min at 37° C. followed by the addition of 10 μl of a solution containing 9% Ficoll, 0.25% bromphenol blue, 0.25% xylene cyanol, and 4% SDS and another 60-min incubation at 37° C. Samples were subjected to electrophoresis in 0.8% agarose gels with TAE buffer (40 mM Tris-Acetate 1 mM EDTA), stained with SYBR-Gold nucleic acid stain (Invitrogen), and exposed to UV light.

Nuclease Site-specific Targeting Assay. The reactions were carried out at 37° C. and contained buffer A and an ATP regeneration system (10 units/ml pyruvate kinase and 3.5 mM phosphoenolpyruvate). Four μM (nt) of a 150-nt long oligonucleotide (rlb1) and 0.67 μM RecAE38K were incubated with the components mentioned above for 10 min followed by the addition of 3 mM ATP and a 20-min incubation. Eight micromolar nucleotides M13mp18 circular dsDNA were added, and the reactions were incubated for another 20 min. Then 48 nM Ref was added. The reactions were stopped by phenol chloroform extraction and ethanol precipitation after 3 h. The resulting pellet was resuspended in EcoRI buffer and cut with EcoRI at 37° C. for 3 h. The digest was stopped by the addition of 10 μA of loading dye (9% Ficoll, 0.25% bromphenol blue, 0.25% xylene cyanol, and 4% SDS) followed by another 30-min incubation at 37° C. Samples were subjected to electrophoresis in 0.8% agarose gels with TAE buffer, stained with SYBR-Gold nucleic acid stain (Invitrogen), and exposed to UV light.

Nuclease Site-specific Targeting Assay to Define Cut Sites. Targeting assays were carried out as described above up until the restriction digest, with the following exception. The 150-nt oligonucleotide used (mcg3) is homologous to bases 6070-6219 of M13mp18 DNA and is 54 nt (top strand) and 50 nt (bottom strand) away from the PstI restriction site. Reactions were digested with PstI at 37° C. for 3 h. The digest was stopped by phenol chloroform extraction and ethanol precipitation. The resulting pellet was resuspended in T4 DNA ligase buffer. Ligations to fluorescently labeled linkers (0.65 μmol) were carried out using 2 μA of T4 DNA ligase and incubating for 1 h at room temperature. Linker 1 (L1) consisted of den7 annealed to mcg2, and linker 2 (L2) consisted of den4 annealed to mcg1. Den7 and den4 were phosphorylated at the 5' OH using polynucleotide kinase (Promega) at 37° C. for 30 min according to the manufacturer's instructions before annealing. The annealing reactions were carried out as described under electrophoretic mobility shift assays. The linkers were designed to have a sticky end complementary to the end created by PstI and a label on the blunt end. The ligation reactions were stopped by ethanol precipitation of the samples. The resulting pellets were resuspended in 90% formamide, 10% EDTA, heated at 95° C. for 10 min, and quick-cooled in an ice-water slurry for 10 min. The samples were then loaded on a 10% denaturing acrylamide sequencing gel and run at 30 watts (1600 V) for 4.5 h in TBE buffer. The fluorescently labeled DNA was then visualized using a Typhoon 9410 Variable Mode Imager (Amersham Biosciences) blue laser at 488 nm.

Structure Determination. P1 Ref (22 mg/ml in 20 mM Tris-HCl, pH 8.0, 200 mM NaCl) was mixed with mother liquor (0.2 M ammonium nitrate, 20% PEG 3350) in a 1:1 ratio and suspended over 1 ml of mother liquor in hanging-drop vapor diffusion experiments to generate crystals. Crystals were transferred to a cryoprotectant solution (0.15 M ammonium nitrate, 22% PEG 3350, 25% ethylene glycol) and flash-frozen in liquid nitrogen before data collection. The structure of the Ref was determined by single-wavelength anomalous dispersion phasing that took advantage of the anomalous scattering of the bound $Zn^{2+}$ ions (Table 2). Diffraction data were collected at a suboptimal wavelength for $Zn^{2+}$ anomalous scattering because it preceded discovery that Ref binds $Zn^{2+}$. However the single wavelength anomalous dispersion phases calculated from the dataset were sufficient to produce an excellent experimental electron density map for model building. The data were indexed and scaled using HKL2000 (Otwinowski and Minor, 1997). Zinc positions were identified, and an initial structure was built using Phenix (Adams et al., 2010). The structure was improved by rounds of manual fitting using Coot (Emsley and Cowtan, 2004) and refinement against the native data set using REFMAC5 (Winn et al., 2001). Coordinate and structure factor files have been deposited at the Protein Data Bank (PDB ID 3PLW).

TABLE 2

Diffraction data and crystal structure solution

| Data collection | |
| --- | --- |
| Wavelength, Å | 0.97856 |
| Space group | P3$_2$21 |
| Unit cell (a, b, c (Å)/α, β, γ (°)) | 71.73, 71.73, 54.24/90, 90, 120 |
| Resolution (last shell), Å | 50-1.4 (1.42-1.40) |
| Reflection measured/unique | 401,946/30,636 |
| Multiplicity | 13.1 (5.6) |
| Completeness (last shell), % | 95.9 (69.4) |
| R$_{sym}$† (last shell), % | 8.6 (43.5) |
| I/σ (last shell) | 29.2 (2.1) |
| Phasing statistics | |
| Resolution, Å | 50-1.4 |
| Figure of merit (before/after density modification) | 0.48/0.66 |
| Refinement | |
| Resolution, Å | 40-1.4 |
| R$_{work}$/R$_{free}$‡, % | 16.3/17.2 |
| Atoms, number/<B factor> | |
| Protein* | 925/13.5 |
| Waters | 127/32.0 |
| Ligands (2Zn$^{2+}$ and 1SO$_4$) | 7/17.6 |
| rms deviation bond lengths, Å | 0.008 |
| rms deviation bond angles, ° | 1.18 |

TABLE 2-continued

Diffraction data and crystal structure solution

| Ramachandran statistics (% most favored/allowed/additionally allowed/disallowed) | 88.3/10.6/1.1/0 |
| --- | --- |

†R$_{sym}$ = ΣΣj|Ij − <I>|/ΣIj, where Ij is the intensity measurement for reflection j and <I> is the mean intensity for multiply recorded reflections.
‡R$_{work}$/R$_{free}$ = Σ||F$_{obs}$| − |F$_{calc}$||/|F$_{obs}$|, where the working and free R factors are calculated by using the working and free reflection sets, respectively. The free R reflections (5% of the total) were held aside throughout refinement.
*Several side-chains were modeled in multiple rotamers/conformations; in cases where atoms have been modeled in multiple conformations, each modeled position is counted in the number of protein atoms (i.e. if a given atom is modeled in two positions it is counted as two protein atoms).

Assay for Quantification of $Zn^{2+}$ Bound to Ref The $Zn^{2+}$ content of wt Ref and of Ref H153A was measured using 4-(2-pyridylazo)resorcinol. 4-(2-Pyridylazo)resorcinol binding to $Zn^{2+}$ causes an increase in absorbance at 490 nm (Hunt et al., 1984). Protein samples were dialyzed against Ref storage buffer (R plus 200 mM potassium glutamate but not containing EDTA) overnight at 4° C. 100 μA of either wt Ref or Ref H153A were incubated with 60 μg of proteinase K for 1 h at 37° C. Then 78.4 μl of that sample was added to 1.6 μl of 5 mM 4-(2-pyridylazo)resorcinol and incubated at room temperature for 20 min, and the absorbances at 490 nm were measured. These measurements were compared with a standard curve of $ZnCl_2$ samples ranging from 1 to 10 μM $ZnCl_2$ in the same buffer.

C. Results

Figure 2:
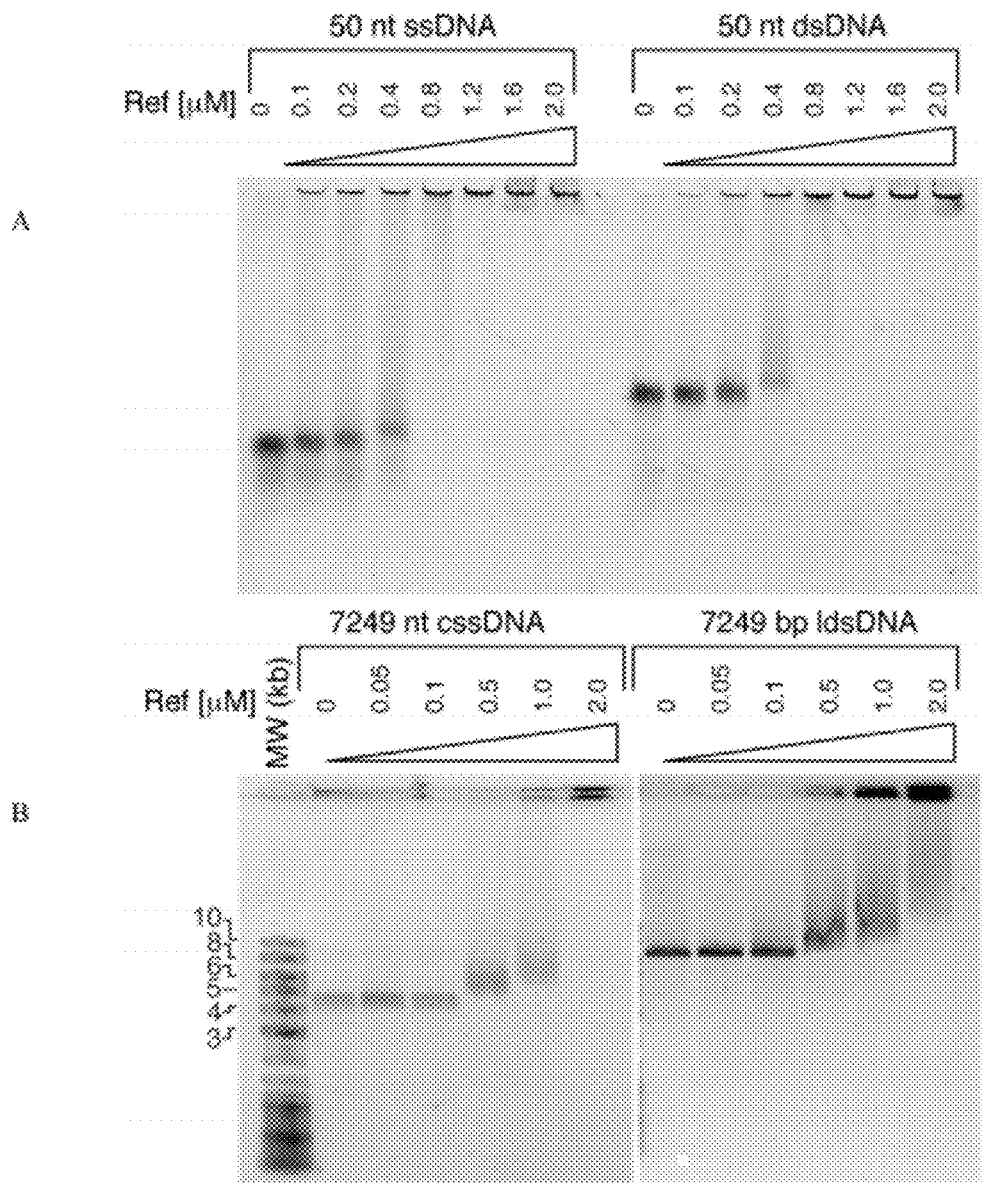
FIG. 2 shows electrophoretic mobility shift assays that were run on an 8% native acrylamide gel for the 50 nt DNA substrates (FIG. 2A) and on a 0.8% agarose gel for the 7249 nt DNA (FIG. 2B). Ref was added at the concentrations indicated in the figure. At high Ref concentrations the complex formed was too large to enter the gel. The results show that Ref binds ssDNA and dsDNA, but does not cleave them in the absence of RecA protein.

To examine the mechanism underlying Ref protein functions with RecA, recombinant Ref protein was expressed and purified by standard methods. The only activity identified for pure Ref protein alone was DNA binding. Ref binds to (but does not cleave) both ssDNA and dsDNA in the absence of any other proteins or nucleotide cofactors (FIG. 2), consistent with results published previously (Lu et al., 1989).

Figure 3:
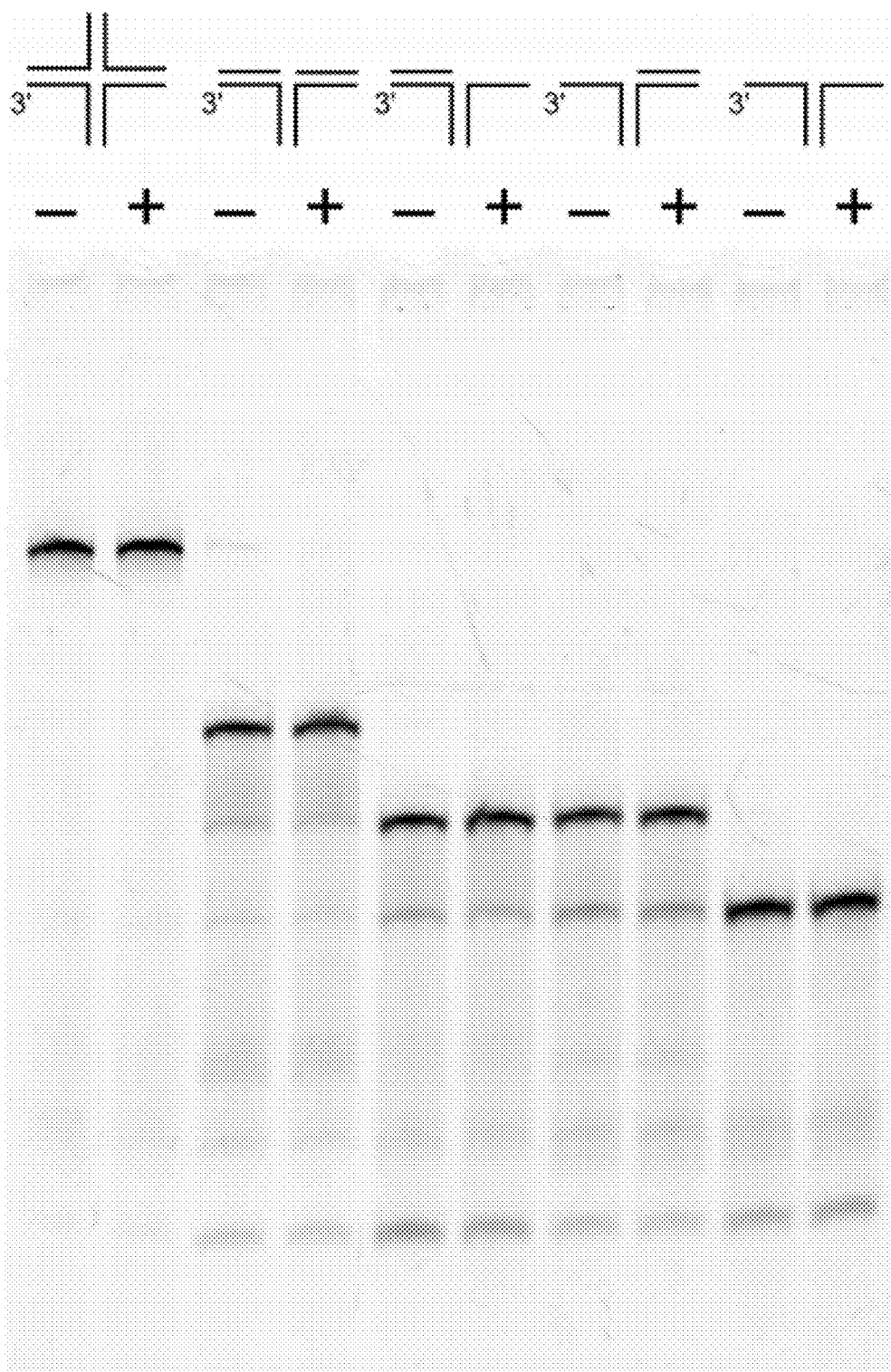
FIG. 3 is an electrophoretic analysis of branched or Holiday junction substrates treated with Ref. The results show no cleavage of the substrates by Ref nuclease. Reactions were carried out in a buffer containing 25 mM Tris-OAc (80% cation), 3 mM potassium glutamate, 10 mM magnesium acetate, and 5% glycerol. DNA substrates were at 25 nM in terms of molecules. Ref was added to 27 nM, and incubations were carried out at 37° C. for 60 min, and stopped by addition of 2.2 mg/ml Proteinase K. The oligonucleotides used to construct the various DNA substrates shown are listed at the bottom of Table 1 (HJ1-4 for the Holliday junction and HJ3 and HJ4+ANP003 and/or ANP004 for the other substrates).

Ref is a RecA-dependent Nuclease. All proteins used in this work, including all Ref protein and Ref variant preps, were tested carefully by themselves for exo- and endonuclease activities on both ssDNA and dsDNA. The screen employs protein concentrations at or above the highest used in this work and incubation times at least equivalent to the longest employed. No nuclease was detected under standard reaction conditions, which includes 24 nM Ref protein. With the wild type Ref, we did note a minor endonuclease activity that nicked about 30% of the supercoiled dsDNA prep but only when we used a 100-fold higher (2.4 μM) concentration and a 2-h incubation (data not shown). No other exo- or endonuclease activities were detectable even at these higher levels of Ref. We further tested a wide range of branched and partially single-stranded DNA substrates for cleavage by wild type Ref protein under standard reaction conditions (FIG. 3). No DNA cleavage was detected for any of these, indicating that Ref does not recognize and cleave a particular type of DNA structure.

Figure 4:
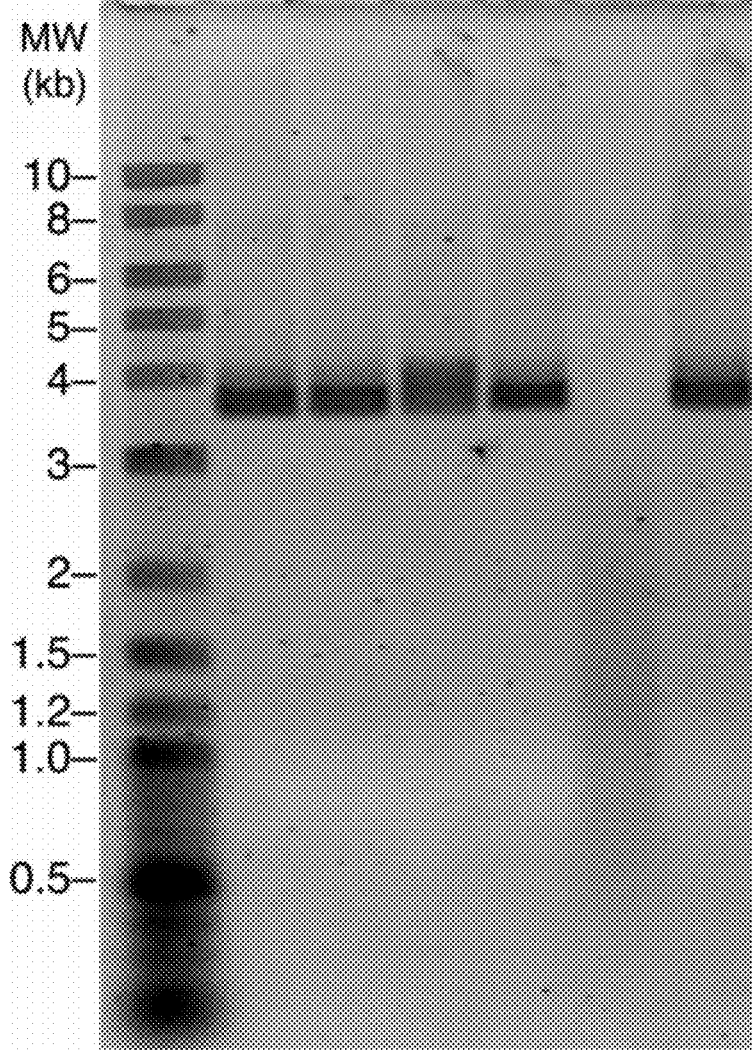
FIG. 4 is an electrophoretic analysis of M13 mp18 circular ssDNA incubated with indicated components showing that Ref degrades ssDNA in a RecA, ATP and $Mg^{2+}$ dependent manner. RecA (2.4 µM) was added to reaction mixtures containing RecA buffer and 4 µM nt DNA for 10 minutes followed by the addition of 3 mM ATP. Ref protein (24 nM) was added 15 minutes later. The reactions were stopped 20 minutes after Ref addition. In lane 6, Ref H153A replaced wt Ref. Here and in other figures illustrating reactions with DNA, the 2-log ladder of duplex DNA fragments is used in the marker lane to provide a point of reference between figures.

When Ref and RecA were introduced to reactions together, the results changed. Incubation of Ref with bacteriophage M13 mp18 circular ssDNA in the presence of RecA protein, ATP, and $Mg^{2+}$ unexpectedly produced extensive degradation of the ssDNA (FIG. 4). All four of the components in the reconstituted system were required for nuclease activity. In particular, the nuclease activity depended on both Ref and active RecA filaments (FIG. 4). ATP is needed to form active RecA nucleoprotein filaments, whereas $Mg^{2+}$ may be used by both RecA and Ref.

Figure 5:
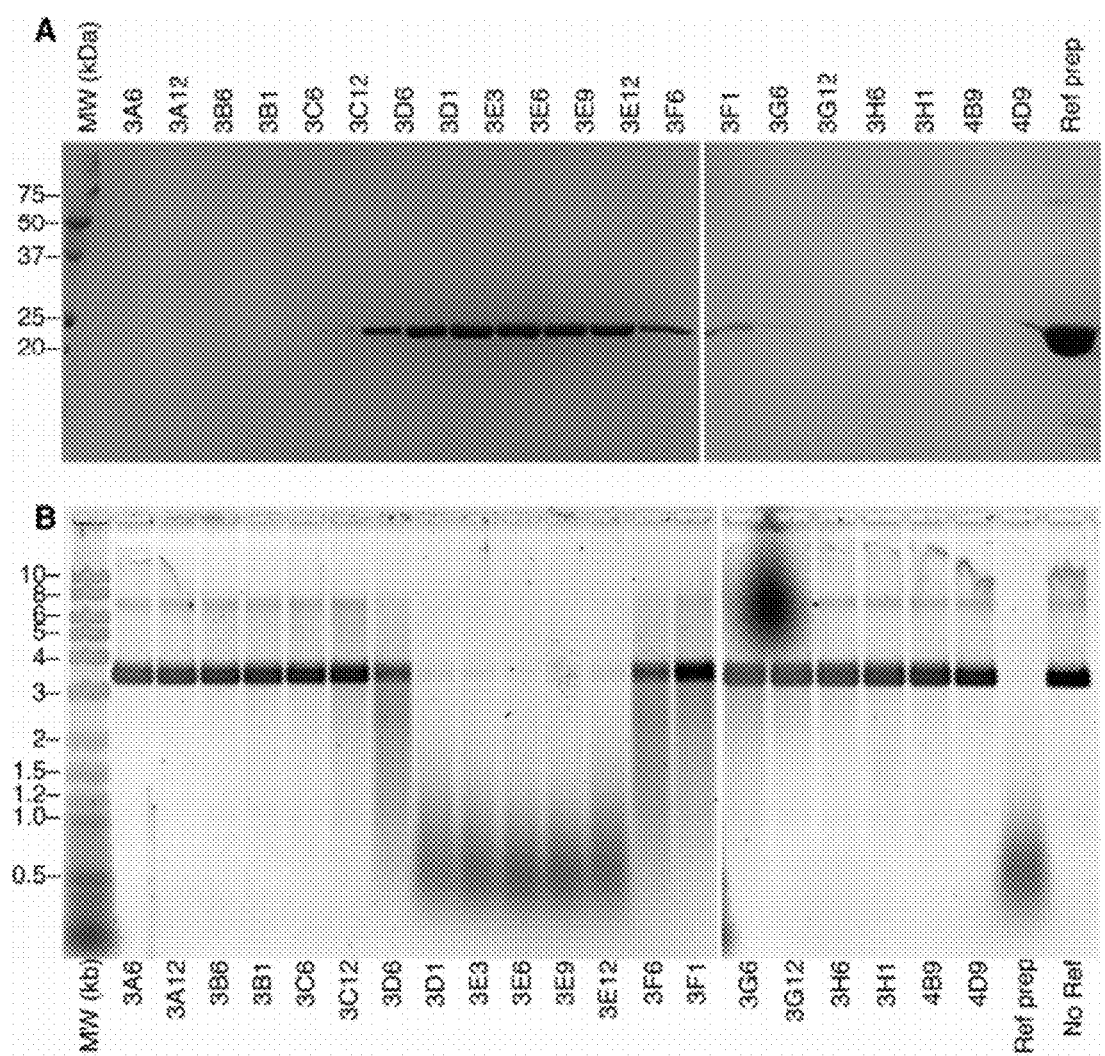
FIG. 5 is an electrophoretic analysis showing that nuclease activity co-elutes with Ref.

The observed RecA-dependent nuclease activity was due to the Ref protein. The activity co-eluted precisely with Ref protein-containing fractions on a gel filtration column (FIG. 5), indicating that the activity was catalyzed by Ref and not a trace contaminant. In addition, as described below, Ref has structural characteristics that identify it as an HNH endonuclease.

The size distribution of the degraded ssDNA in the RecA-dependent reaction suggested random cleavage, and the average length of fragments decreased with time. After 20 min of incubation, the average fragment size was about 1.2 kb, indicating that about 6 cleavage events have occurred per DNA molecule (3 nM total cleavage events) in the presence of 24 nM Ref protein. This indicates a turnover of just under 0.01 cleavage events per minute.

Ref-mediated DNA cleavage in the presence of RecA protein was selective in that ssDNA was cleaved but RecA-bound dsDNA was not. No degradation of dsDNA was detected under any set of conditions, including conditions (low pH or longer preincubation with RecA to allow filament nucleation) in which saturating levels of RecA protein were demonstrably bound as indicated by RecA-mediated ATP hydrolysis (data not shown).

Figure 6:
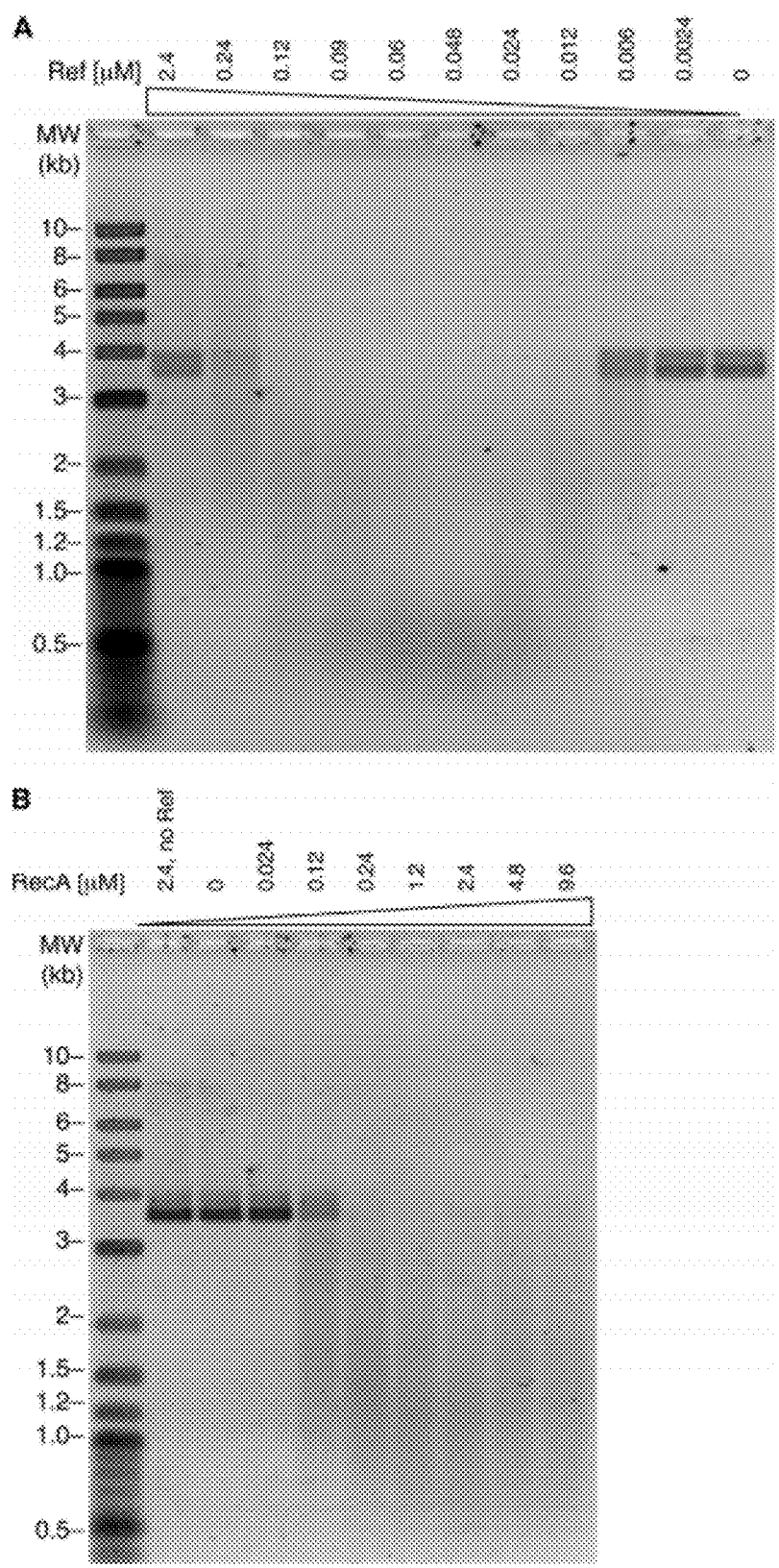
FIG. 6 shows the results of nuclease assays carried out as described in Example 1. The results show the dependence of Ref ssDNA nuclease activity on RecA and Ref concentrations. For FIG. 6A, RecA concentration was constant at 2.4 µM and Ref was added as indicated. For FIG. 6B, RecA concentrations were varied as indicated in the figure, and 48 nM Ref was added.

Ref nuclease activity on ssDNA was observed under all conditions under which RecA filaments formed. Optimal concentrations of Ref protein are far substoichiometric to both RecA and ssDNA nucleotides (about one Ref monomer to 100 RecA monomers) (FIG. 6A). At Ref concentrations approaching RecA concentrations, nuclease activity is inhibited (FIG. 6A). The direct binding of Ref to DNA could possibly inhibit RecA filament formation and preclude Ref activation. If the RecA protein concentration is reduced to levels insufficient for normal RecA filament formation but equivalent to the standard concentrations of Ref protein we used, Ref nuclease activity was again suppressed (FIG. 6B).

Figure 7:
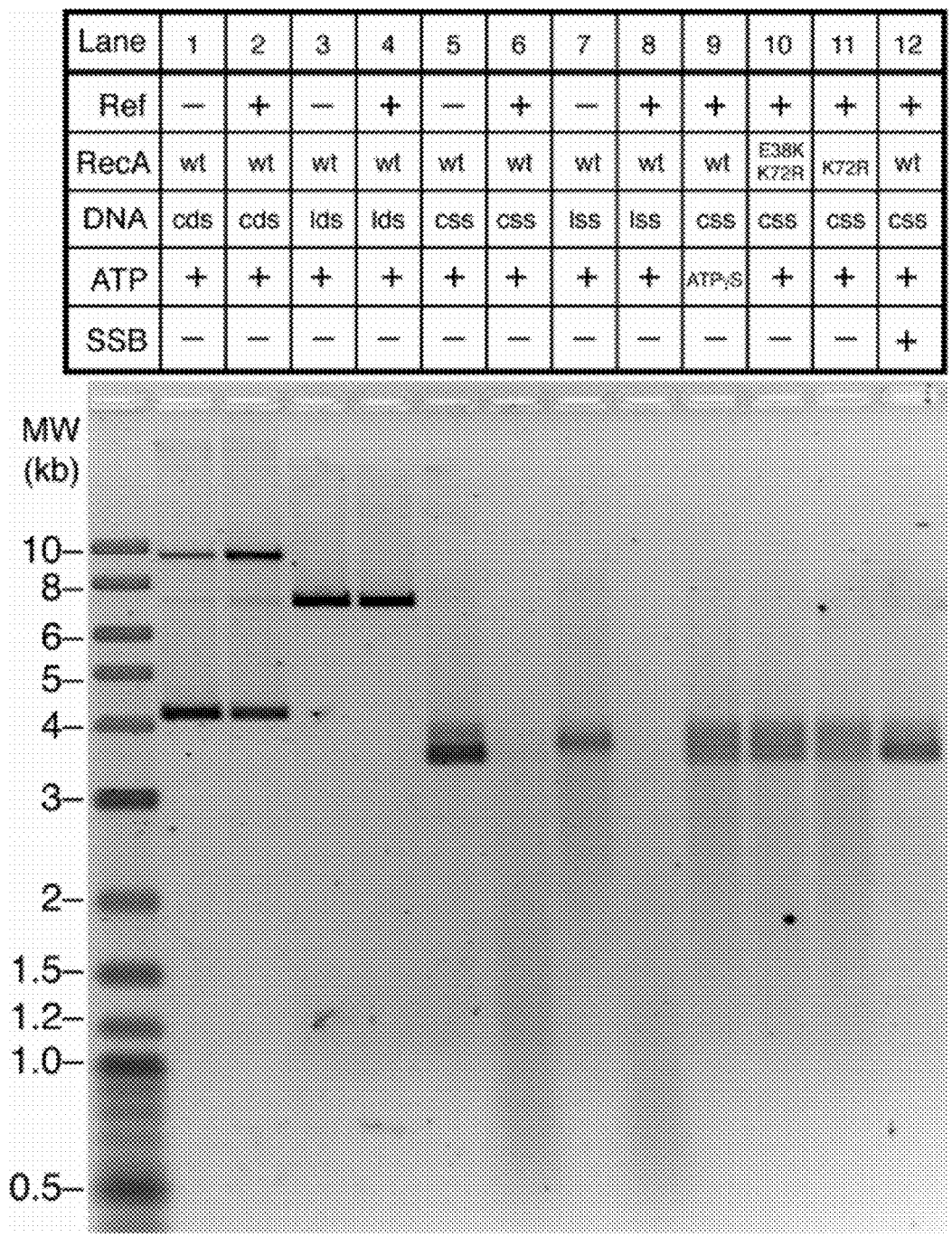
FIG. 7 is an electrophoretic analysis of linear ds DNA (lds), supercoiled dsDNA (cds), circular ssDNA (css), and linear ssDNA (lss) substrates and RecA variants used as indicated, showing the activity of Ref/RecA on the different DNA substrates and with ATPase-deficient RecA variants. Reaction conditions and protocols are as described above in regards to FIG. 4. In lane 12, 0.4 µM single-stranded DNA binding (SSB) was added to the DNA immediately before RecA was added. The linear ssDNA (lanes 7 and 8) was prepared by restriction digestion of circular M13mp18ssDNA to which a short oligonucleotide had been annealed at the restriction site. The extensive secondary structure of M13mp18 ssDNA led to some nonspecific restriction digestion at other sites, producing some smearing of the DNA band.
Figure 8:
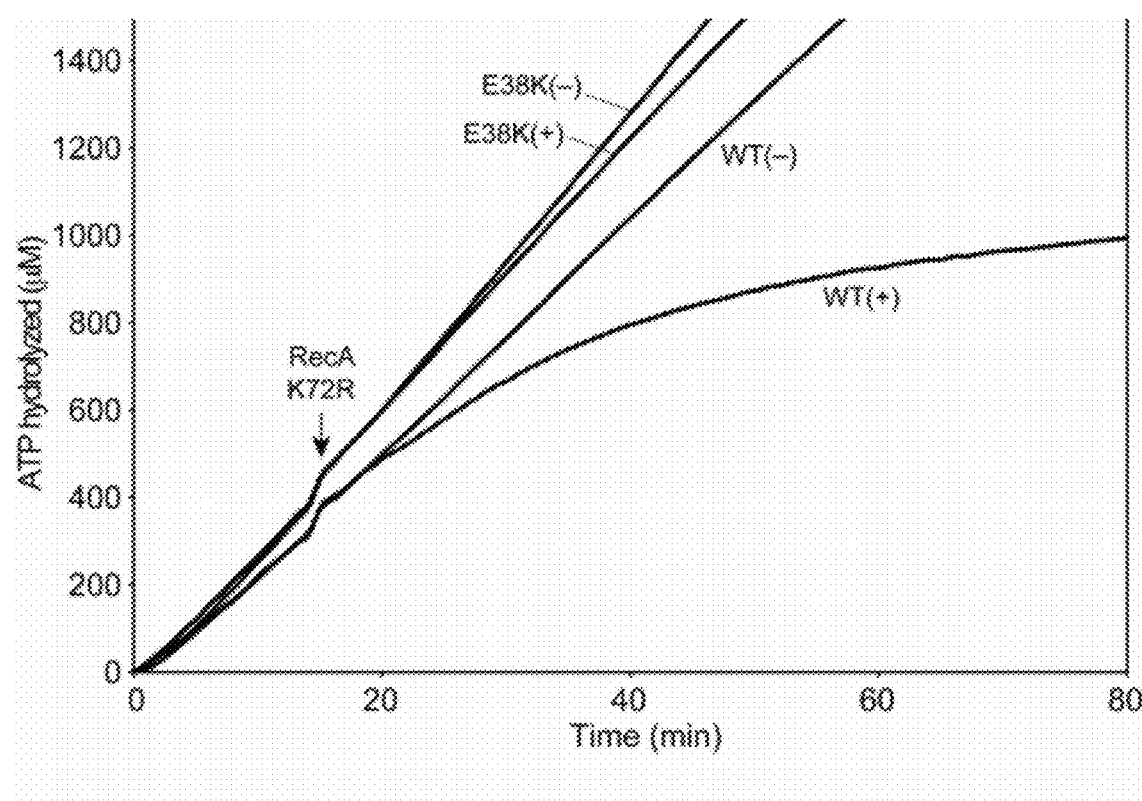
FIG. 8 is a coupled ATPase assay for real time measurement of RecA-mediated ATP hydrolysis, showing that the RecA E38K protein is less dynamic than the wild type protein. Pairs of reactions were carried out at 37° C. and contained 3 µM (nucleotides) M13 mp18 ssDNA, and 1.5 µM either RecA WT or RecA E38K. ATPase reactions were initiated with 3 mM ATP and 0.3 µM SSB. After 15 minutes, one reaction in each pair was challenged with the addition of 1.5 µM RecA K72R (a mutant RecA that binds but does not hydrolyze ATP). RecA protein that dissociates from the RecA filaments cannot be replaced with ATPase-proficient RecA protein after the challenge. The ATPase rate drops for the wild type protein due to RecA subunit dissociation, but the ATPase activity of the RecA E38K mutant protein is unaffected.

The RecA dependence of the nuclease activity implies an interaction between RecA and Ref. In principle, the RecA-dependent nuclease reaction could occur at a RecA filament end. Alternatively, it could involve DNA strands exposed in the RecA filament groove. We first examined the effect of RecA mediated ATP hydrolysis. DNA degradation is reduced when ATP is not hydrolyzed by RecA. This is true for wild type RecA protein incubated with the non-hydrolyzable ATP analog, ATPγS, (FIG. 7, lane 9), and when ATPase-deficient RecA mutants such as RecA K72R and RecA E38K K72R are used (FIG. 7, lanes 10-11). Inasmuch as ATP hydrolysis is coupled to RecA dissociation at the 5'-proximal filament end, this could indicate that Ref-mediated cleavage occurs at the disassembling end of a filament. However, the RecA E38K mutant protein, which disassembles much less than the wild type protein (FIG. 8), promoted the Ref cleavage reaction at least as well and sometimes better (20-30% increase in some assays (data not shown)) than the wild type RecA. The RecA E38K mutant, thus, replaced the wild type RecA in many assays with Ref.

Figure 9:
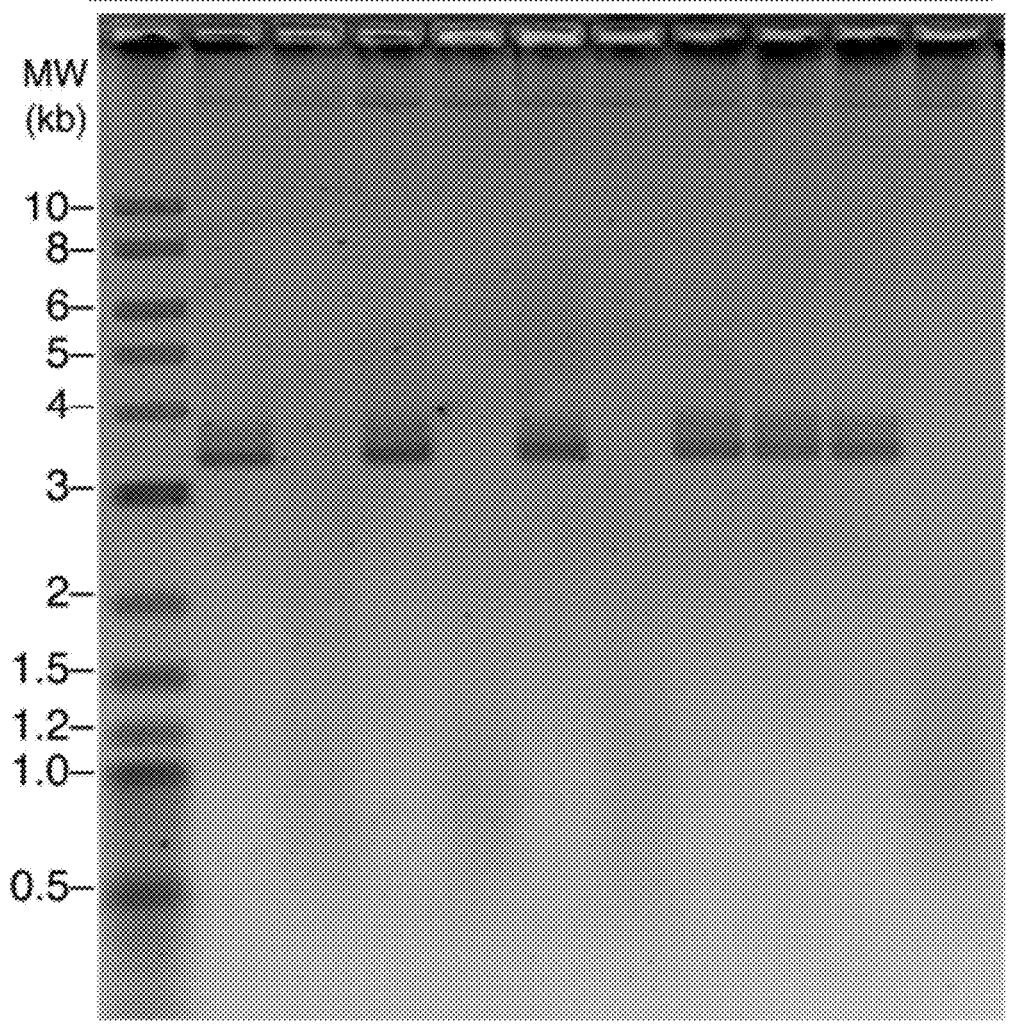
FIG. 9 shows the results of nuclease assays that were carried out as described in Example 1. UmuD1 (7.2 µM), LexA (7.2 µM), LexA S119A (7.2 µM) or DinI (16.8 µM) were added immediately before RecA was added. The presence or absence of Ref is indicated in the figure. The results show that the non-cleavable LexA mutant inhibits Ref nuclease activity.

We also examined the effect of proteins that bind in the RecA filament groove. Ref-mediated nuclease activity is blocked by a non-cleavable variant of the LexA protein (S119A) that binds well enough to active RecA filaments to inhibit DNA strand exchange (Harmon et al., 1996), but not by the DinI protein, the non-cleavable UmuD1 protein, or the wild type LexA protein (FIG. 9). All of these proteins appear to bind in distinct (and sometimes transient) ways to the major groove of a RecA filament (VanLoock et al., 2003). When single-stranded DNA binding protein is incubated with DNA before RecA is added, so as to inhibit RecA binding, Ref does not exhibit nuclease activity (FIG. 7, lane 12).

The X-ray Crystal Structure of Ref Reveals a Novel HNH-family Nuclease. A sequence data base search revealed only a small number of uncharacterized Ref homologs. These included six close homologs (>90% identity) encoded by bacteriophages or prophages related to P1 and three additional bacterial genes encoding more distantly related proteins. A sampling of these is presented in FIG. 10A. The bacterial proteins, such as those from *Salmonella enterica* subsp. *enterica serovar* Newport strain SL317, ~65% identical, and *Bordetella avium* may be parts of cryptic prophages.

Comparison of this small sampling of Ref sequences revealed the presence of invariant Cys-Xaa-Xaa-Cys, Cys-Xaa-Xaa-His, and His-His motifs. Similar motifs are known to be involved in divalent metal binding (generally $Zn^{2+}$) in other proteins, which led us to test whether Ref binds $Zn^{2+}$. $Zn^{2+}$ was associated with purified Ref at a 1.6:1 metal:protein ratio (Table 3). Because chelating agents were included during purification of Ref, these $Zn^{2+}$ ions are likely to be stably bound to the protein.

TABLE 3

Table $Zn^{2+}$ quantification

| Protein Sample | Protein [μM] | $[Zn^{2+}]$, μM | $[Zn^{2+}]$:[protein] | Average $[Zn^{2+}]$:[protein]* |
|---|---|---|---|---|
| wt Ref | 2.66 | 4.63 | 1.74 | 1.59 (±0.16) |
|  | 3.37 | 4.79 | 1.42 |  |
|  | 2.39 | 3.84 | 1.61 |  |
| Ref H153A | 2.47 | 4.37 | 1.77 | 1.55 (±0.20) |
|  | 3.45 | 5.19 | 1.50 |  |
|  | 2.84 | 3.93 | 1.38 |  |

*Average of three independent experiments as represented in the three columns to the left.

Figure 10:
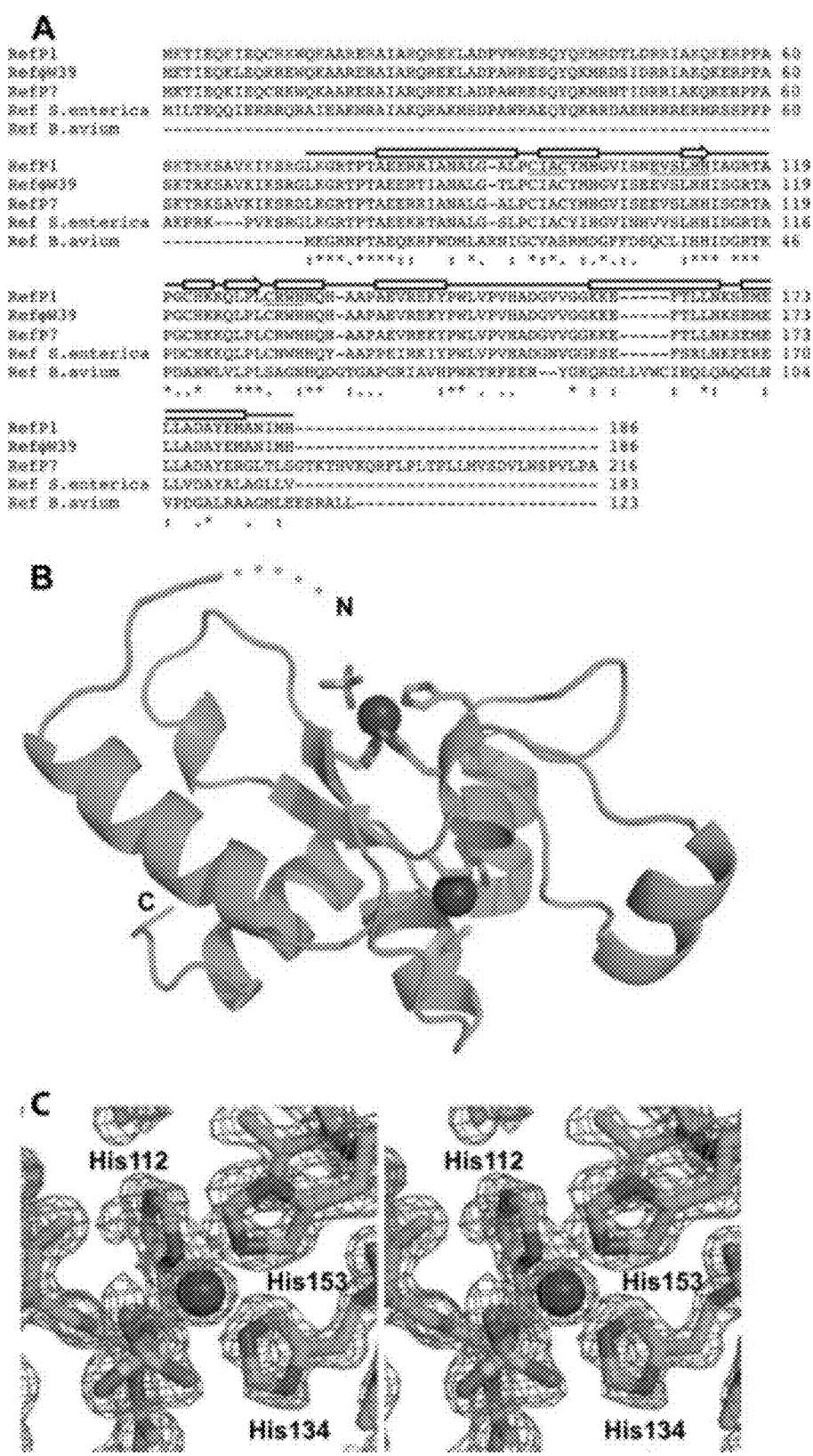
FIG. 10 shows the structure of bacteriophage P1 Ref protein.

A crystallographic approach was taken to better understand the structure and function of Ref. Crystals of Ref that diffracted to 1.4 Å resolution were produced, and the structure was determined by single-wavelength anomalous dispersion phasing that took advantage of anomalous scattering by the bound $Zn^{2+}$ ions (Table 2). Consistent with the solution $Zn^{2+}$ binding studies, the crystallographic asymmetric unit contained a single Ref protein bound to 2 $Zn^{2+}$ ions (FIGS. 10, B and C).

Figure 11:
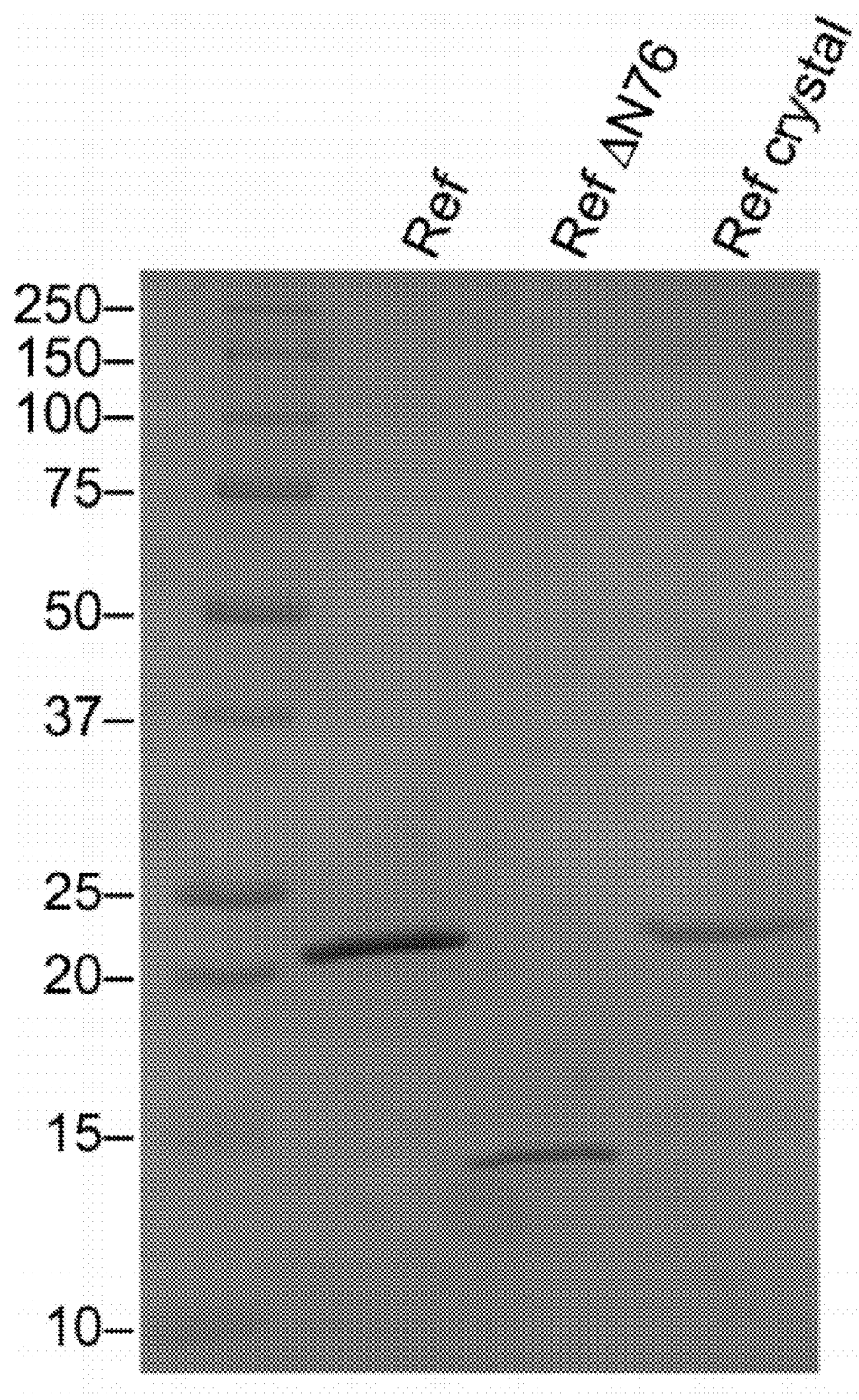
FIG. 11 is an SDS-polyacrylamide gel showing purified Ref protein in the first lane, Ref ΔN76 in the second lane, and Ref protein from one crystal grown under the same conditions as the crystals used for Ref structure determination.

Ref folds as a globular protein, with a central two-stranded β-hairpin that is sandwiched between several α-helical and extended loop elements (FIG. 10B). Electron density for the N-terminal 76 residues was absent, indicating that it may be a flexible element. A careful search for difference density did not reveal any additional structural information about the missing N-terminal amino acids. To test whether the N terminus of the protein remained intact after crystallization, we washed and dissolved several crystals and subjected them to SDS acrylamide electrophoresis. The crystallized protein was completely intact (FIG. 11).

Figure 12:
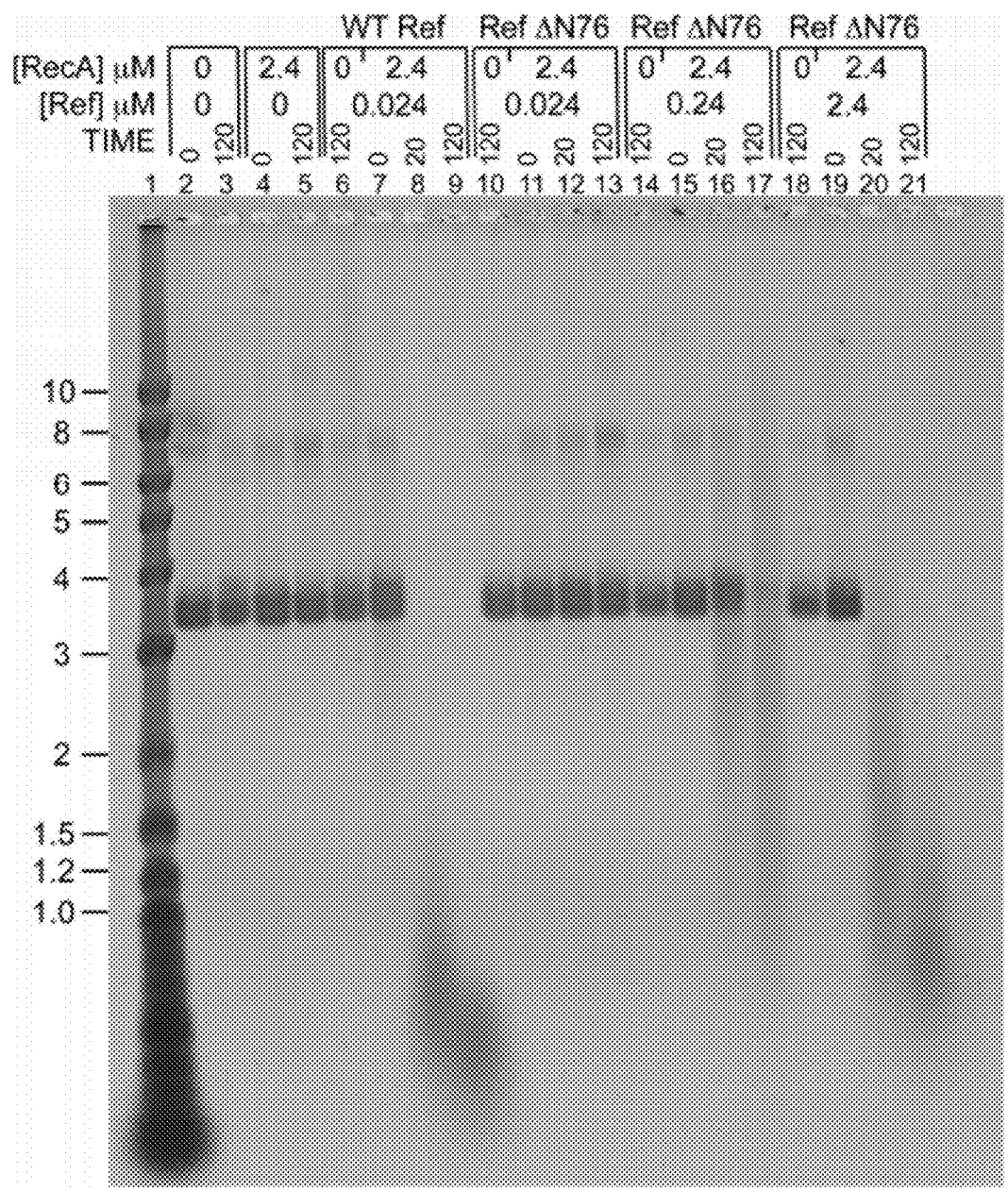
FIG. 12 is an electrophoretic analysis showing that the Ref ΔN76 mutant protein exhibits reduced activity for RecA-dependent cleavage of ssDNA. Reactions were carried out as described in Example 1, with the concentrations of RecA and Ref protein indicated at the top of the figure. The indicated incubation times are in minutes. As in other figures illustrating reactions with DNA, the 2-log ladder of duplex DNA fragments from New England Biolabs is used in the marker lane to provide a point of reference between figures.

To test the functional importance of the N terminus, we constructed a deletion mutant of Ref that lacked the 76 N-terminal amino acids and purified it. It proved to be devoid of Ref-mediated nuclease activity on ssDNA under normal reaction conditions (FIG. 12, lanes 11-13). Some RecA-dependent ssDNA cleavage was seen at much higher concentrations of the mutant Ref protein (10× and 100×; FIG. 12, lanes 14-21). Ref ΔN76 was completely deficient in DNA binding to a 50-mer oligonucleotide up to a concentration of 2.4 μM using the assay shown in FIG. 4 (data not shown). This indicates that the disordered N-terminal domain plays an essential role the DNA binding activity of Ref and also enhances the RecA-dependent nuclease activity. We note that these N-terminal 76 amino acid residues represent a very highly charged part of the protein. Of the 76, 25 are amino acids with a positive charge (Arg or Lys (FIG. 15A)), and another 9 are negatively charged (Glu or Asp). Interestingly, the apparent homolog from *B. avium* has lost 75 of these 76 amino acid residues (FIG. 10A).

The central β-hairpin element of Ref is threaded through the core of the protein and presents ligands that define the $Zn^{2+}$-binding sites. The first binding site is composed of three His residues that are presented by the first β-strand of the hairpin, an adjacent α-helix, and a loop that is C-terminal to the hairpin (FIG. 10B). Interestingly, this $Zn^{2+}$ is also liganded by a $SO_4^{2+}$ ion, indicating that the $Zn^{2+}$ bound at this site is solvent-exposed. The second site is composed of three Cys and one His residues from helical and loop elements in the structure. This second $Zn^{2+}$ ion is entirely buried within the protein core.

Figure 13:
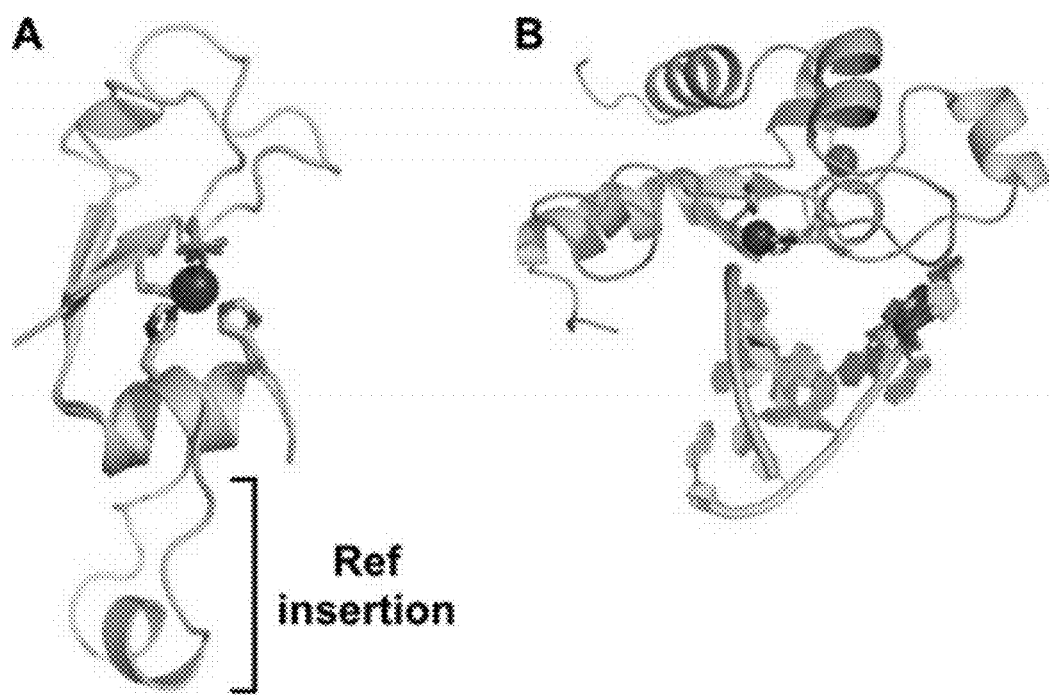
FIG. 13 shows the Ref protein active site. The drawing of the Ref crystal structure (FIG. 13A) reveals an active site similar to HNH family endonucleases. Comparison of the ββα folds of Ref and E9 DNase is shown. An insertion in Ref relative to E9 DNase is labeled.

Comparison of the Ref structure to other proteins in the Protein Data Bank using automated structure-comparison software failed to reveal any similar structures. However, we noticed that a motif in Ref bore similarity to an element in the HNH family of nucleases. HNH family members are defined by the presence of ββα-metal core elements in which residues from the β-hairpin/α-helical structure form a metal-binding site. Outside of this core, HNH enzymes are structurally diverse. The HNH family includes a number of bacteriophage-encoded homing endonucleases among others (Stoddard, 2005). Overlaying the β-hairpin core of Ref and the colicin E9 HNH DNase (Mate and Kleanthous, 2004) revealed a striking similarity in the ββα-metal core between the two proteins (FIG. 13A). In both cases, the three $Zn^{2+}$ binding His residues superimpose nearly identically, and a fourth $Zn^{2+}$ ligand ($SO_4^{2-}$ or $PO_4^{3-}$) is also nearly identically positioned. Outside of the ββα-metal core, the Ref and the E9 DNase fold lack tertiary or topological similarity. Even within the ββα-metal core there are differences. For E9 DNase, the second and third $Zn^{2+}$ binding His residues are both presented from the α-helix of the ββα fold. In contrast, for Ref the first of these His residues is from the helix, but the second (His-153) is presented by a extended loop element. This split arrangement of His residues distinguishes Ref from other HNH family members, partially explaining the lack of previous recognition of a possible nuclease function for Ref.

Superposition of the ββα-metal core folds of Ref and the DNA-bound form of the E9 DNase allowed a DNA-bound structure of Ref to be modeled (FIG. 13B). This model predicts that the scissile phosphate would be positioned where the $SO_4^{2-}$ ion is observed in the Ref structure and that the $Zn^{2+}$ binding His residues also form portions of the nuclease active site. To test this model, a Ref variant in which His-153 is substituted with Ala was constructed, purified, and found to lack all nuclease activity (FIG. 4). The inactivity of this Ref H153A mutant is not due to a loss of the $Zn^{2+}$ ion in the active site (Table 3), suggesting that the His-153 residue itself is important for catalysis. In addition, Ref H153A appears to be properly folded, as determined by circular dichroism (FIG. 1). Interestingly, elements that are important for DNA binding in E9 (Garinot-Schneider et al., 1996) are absent in the core Ref structure, further suggesting that the DNA binding activity is embedded in the N-terminal amino acids.

HNH-family nucleases are defined by the ββα-metal core fold in which a central His or Asp residue is immediately flanked by an N-terminal Asp or His residue and at some distance by a C-terminal His, Asp, or Glu residue (Mehta et al., 2004). For P1 Ref, this sequence is -His-His-(9 residues)-His- for residues 112-123. HNH-family members generally also have conserved Cys-Xaa-Xaa-Cys sequence motifs N- and C-terminal to this central sequence cluster that are used for binding metals; a His residue can substitute for one of the Cys residues in these motifs. P1 Ref also has such motifs (Cys-11e-Ala-Cys (residues 96-99) and Cys-Arg-Trp-His (residues 130-133)). We note that the apparent homolog encoded by *B. avium* (FIG. 10A) has replaced a Cys with a Ser residue in both of these motifs. Mehta et al. (2004) have defined 8 subclasses of HNH-family nucleases by comparing the sequences of 323 proteins using ClustalW. Comparing P1 Ref to these eight subclasses indicated that Ref did not fit into any of the published categories. Thus, we propose that Ref defines a new subclass of HNH-family nucleases.

Figure 14C:
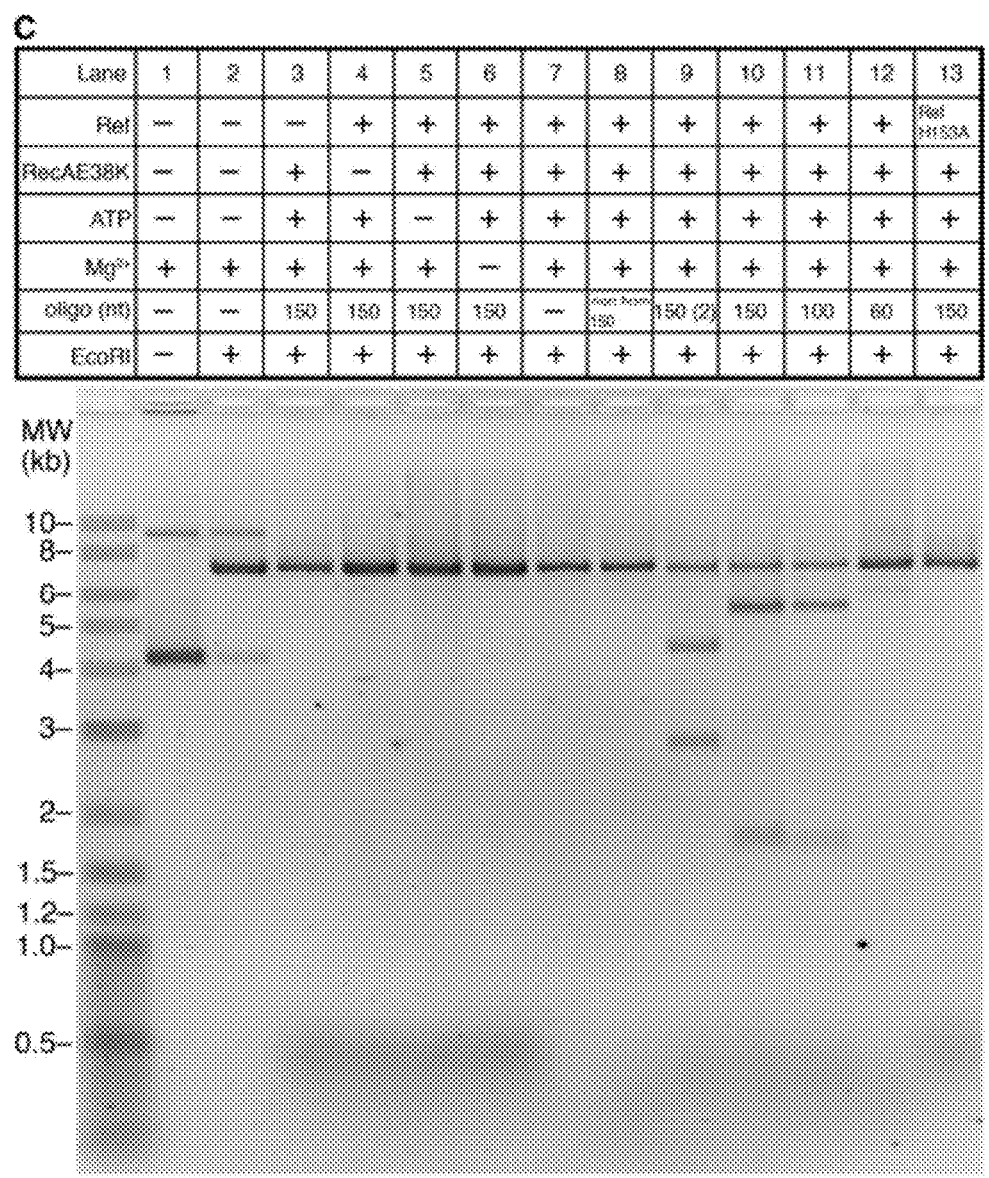
FIG. 14C is electrophoretic analysis of reactions carried out as shown in FIG. 14A. Components were omitted from the reactions as indicated above the pane; RecA E38K was used instead of wt RecA because it produced a slightly increased product yield. In lane 8 a 150-nt oligo that was not homologous to M13mp18 was used. In lanes 9 and 10, two 150-nt oligos complementary to M13mp18 at different locations were used (see FIG. 14B). In lane 11, a 100-nt oligo complementary to M13mp18 at the same location as the 150-nt oligo in lane 10 was used. In lane 12, a 60-nt oligo homologous to M13mp18 at a different location replaced the 150-mer. In lane 13, Ref H153A replaced wt Ref.

Ref Activity Can Be Restricted to D-loops Created by RecA; Oligonucleotide-directed Introduction of Double-strand Breaks. During DNA strand exchange, the RecA protein can bind up to three strands of DNA (Cox, 2003). As shown in FIG. 14, Ref will cleave both strands of a duplex DNA at the site of a D-loop formed by a RecA-coated oligonucleotide complementary to that site. In this experiment, the RecA E38K mutant protein replaced the wild type RecA protein as it consistently produced a 20-30% enhancement of activity relative to the wild type RecA protein (data not shown). Lanes 9-12 of FIG. 14C, employing four oligonucleotides targeted to three different sites in the duplex DNA circle, make two points. First, restriction enzyme analysis demonstrates that the Ref-induced breaks in the circular double stranded DNA occur where the RecA-bound oligonucleotide invaded the duplex DNA to form a D-loop. This result demonstrates the targeting potential of the Ref/RecA system. It also provides additional evidence that Ref is activated for cleavage by direct interaction with RecA protein filaments. Second, the length of the oligonucleotide influences RecA activation of Ref. The best cleavage is seen with the two 150-mers. A 100-mer targeted to the same site as one of the 150-mers is nearly as effective. Cleavage efficiency drops off substantially for the 60-mer, corresponding to the decreased stability of RecA filaments on the shorter oligonucleotide (McIlwraith and West, 2001). Like the ssDNA nuclease activity, targeted dsDNA nuclease activity depends on RecA, ATP, $Mg^{2+}$, and the presence of a homologous oligonucleotide (FIG. 14C). The Ref H153A variant was again inactive.

Figure 15A:
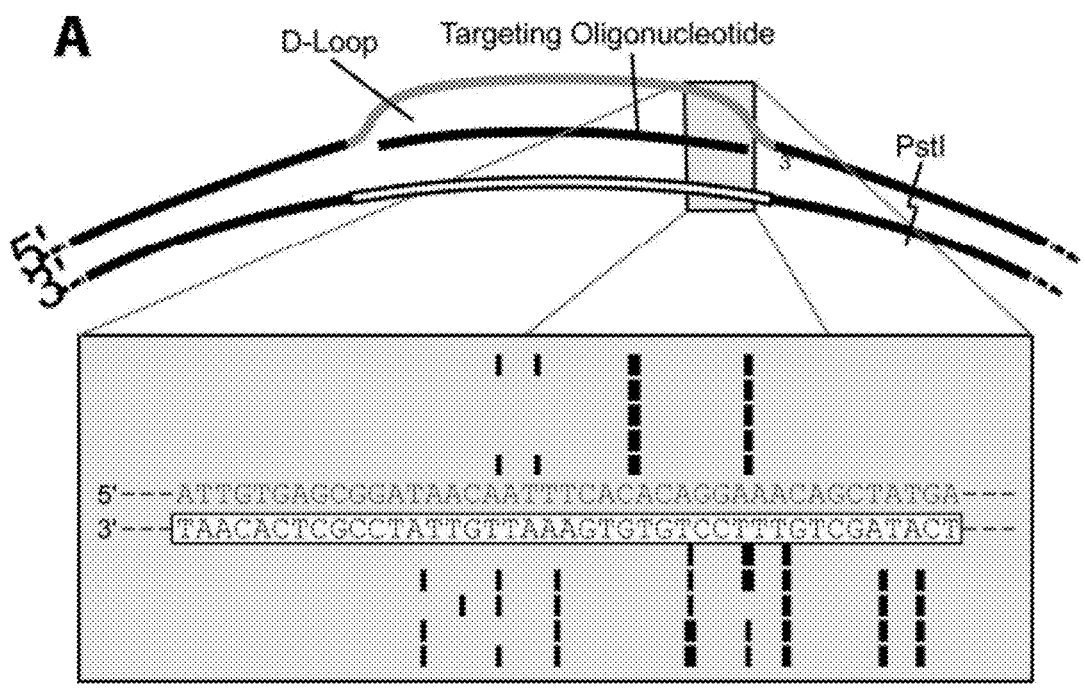
FIG. 15A is a diagram showing cleavage sites detected in five independent targeted cleavage experiments. The duplex DNA sequences corresponding to the 3' end of the 150-mer targeting oligonucleotide are shown in the gray box, corresponding to the region containing the detected Ref-mediated cuts in the M13mp18 DNA. The thickness of the marks corresponds approximately to the intensity of the bands on the sequencing gel. Each row of marks represents one independent experiment.

We determined sites of DNA cleavage within the region targeted by one of the 150-mer oligonucleotides, cutting the reaction product at a nearby restriction site (PstI) and ligating a labeled linker to the resulting fragment. A gel allowing dideoxy sequencing-like resolution reveals that Ref-mediated cuts are found at multiple locations, all relatively close to the 3' end of the invading oligonucleotide (FIG. 15A). We note that the method employed would eliminate signals from distal cleavage sites for any DNA that was cleaved twice on the same strand of the D-loop and, thus, may bias the results toward detection of 3' end-proximal events. However, the results clearly indicate that cleavage can occur at multiple locations within the D-loop. Preferred cleavage sites were evident, although the mechanistic basis of the pattern is not yet understood. The patterns also indicate that Ref-mediated introduction of double-strand breaks does not necessarily generate blunt ends.

D. Discussion

There are four major conclusions to this work. First, the bacteriophage P1-encoded Ref protein is an endonuclease, with the novel property that nuclease function is entirely dependent on the presence of active RecA nucleoprotein filaments. Second, Ref is not simply activated by RecA. Where cleavage locations can be correlated with RecA locations (FIG. 14), Ref cleaves DNA where RecA protein is bound. Thus, the work defines a new function for RecA nucleoprotein filaments, that of co-nuclease. Third, our structural analysis indicates that Ref protein defines a new subfamily of HNH endonucleases. Finally, the Ref/RecA system can be used to introduce targeted double-strand breaks at any chosen location in an oligonucleotide-directed manner. The enhanced RecA-dependent recombination observed in vivo when Ref is present does not reflect regulation of RecA. Instead, through Ref, bacteriophage P1 employs a strategy for the stimulation of homologous recombination that is seen during meiotic recombination in eukaryotes, the directed generation of double-strand breaks.

Multiple experiments indicate that the observed nuclease activity is due to Ref and not to a contaminating nuclease activity. All protein preparations used in this study were carefully tested and found free of exo- or endonuclease activity on circular or linear single- or double-stranded DNA under standard reaction conditions. The observed nuclease activity coelutes with the Ref protein on a size exclusion column. Finally, the structure of the Ref protein identifies it as a novel HNH endonuclease.

These results further broaden the already long list of functions for RecA filaments to include co-nuclease. The Ref protein cleaves only where RecA protein is bound to DNA. The reaction is enhanced if the RecA filament actively hydrolyzes ATP. In principle, Ref could cleave at a filament end or in the RecA filament groove. The enhancement by ATP hydrolysis might suggest a link to end-dependent RecA filament dissociation. However, we currently favor a mechanism in which cleavage occurs in the filament groove for two major reasons. First, the Ref-mediated cleavage reaction is also enhanced when the RecA E38K mutant protein replaces the wild type RecA. The filaments formed by the E38K mutant protein are much less dynamic than those of the wild type protein, exhibiting no measurable dissociation in a standard challenge assay when they are bound to ssDNA. Second, the Ref-mediated cleavage reaction is completely inhibited by the LexA S119A mutant protein, which binds stably in the RecA filament groove. RecA-mediated ATP hydrolysis is not limited to the ends of RecA filaments (Brenner et al., 1987), but occurs throughout the filament. Conformation changes associated with the ATP hydrolytic cycle may play some role in the Ref nuclease reaction. A structure of RecA bound to DNA in the presence of ATP has appeared (Chen et al., 2008). However, the core domain of RecA is closely related to helicases, in which substantial conformational changes are associated with ATP hydrolysis (Geiselmann et al., 1993). For RecA, little is known about the structural changes associated with ATP hydrolysis or the status of bound DNA strands at different stages of that cycle.

The Ref protein features a core structure with a clear relationship to HNH endonucleases. Elimination of an active site His residue (His-153) eliminated Ref function. The 76 N-terminal residues of Ref were disordered in the structure. This region of the protein features 34 charged amino acid side chains (25 Lys or Arg), and results so far indicate that it is the region responsible for the DNA binding activity of Ref.

Figure 15B:
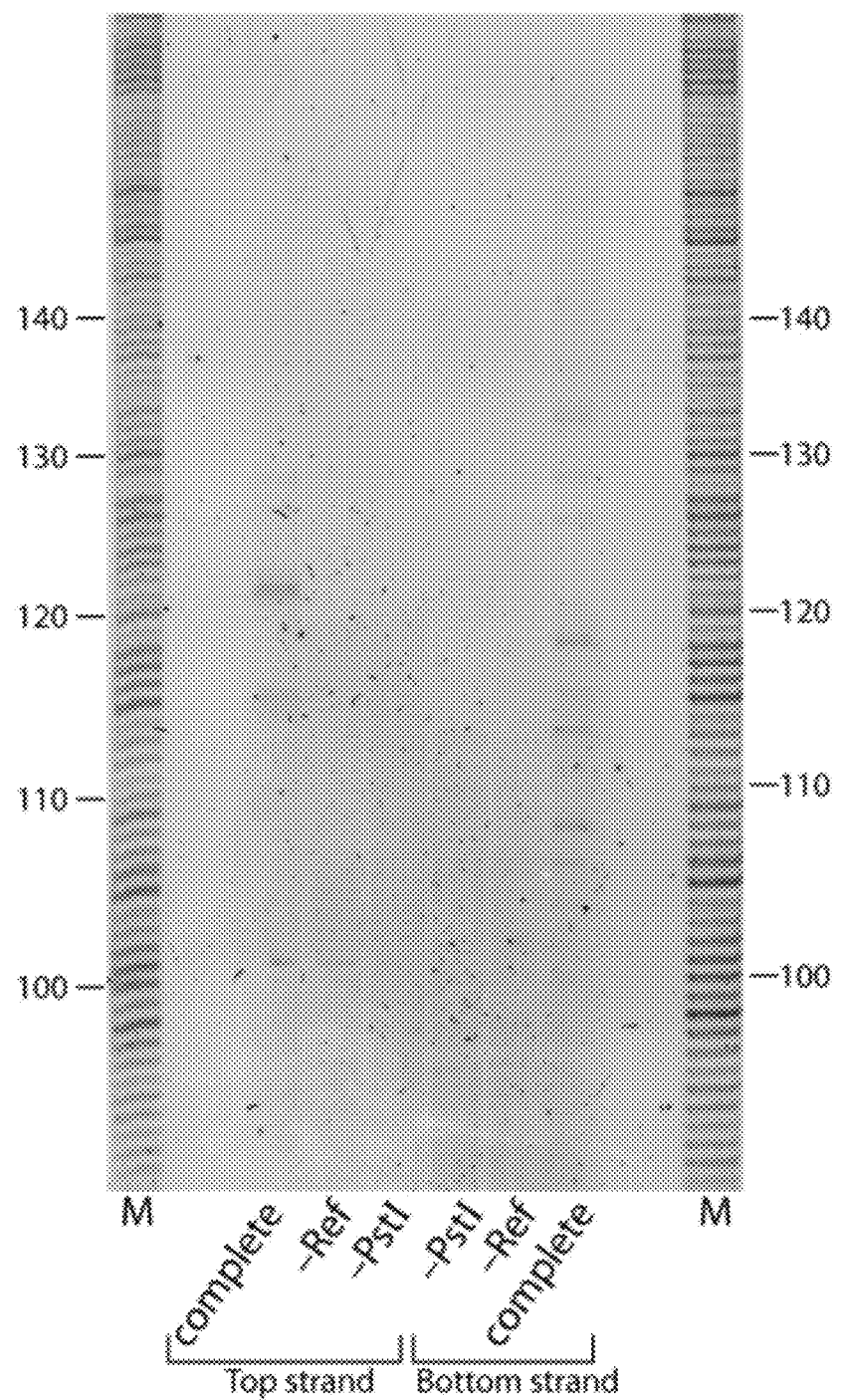
FIG. 15B shows the sequencing gel results for a site-determination experiment. Reactions were carried out as described in Example 1. After Ref-mediated cleavage of targeted DNA within D-loops, the DNA was isolated and cleaved with PstI restriction endonuclease. A labeled oligonucleotide was ligated to the cleaved end followed by sizing of the products on a sequencing gel.
Figure 16:
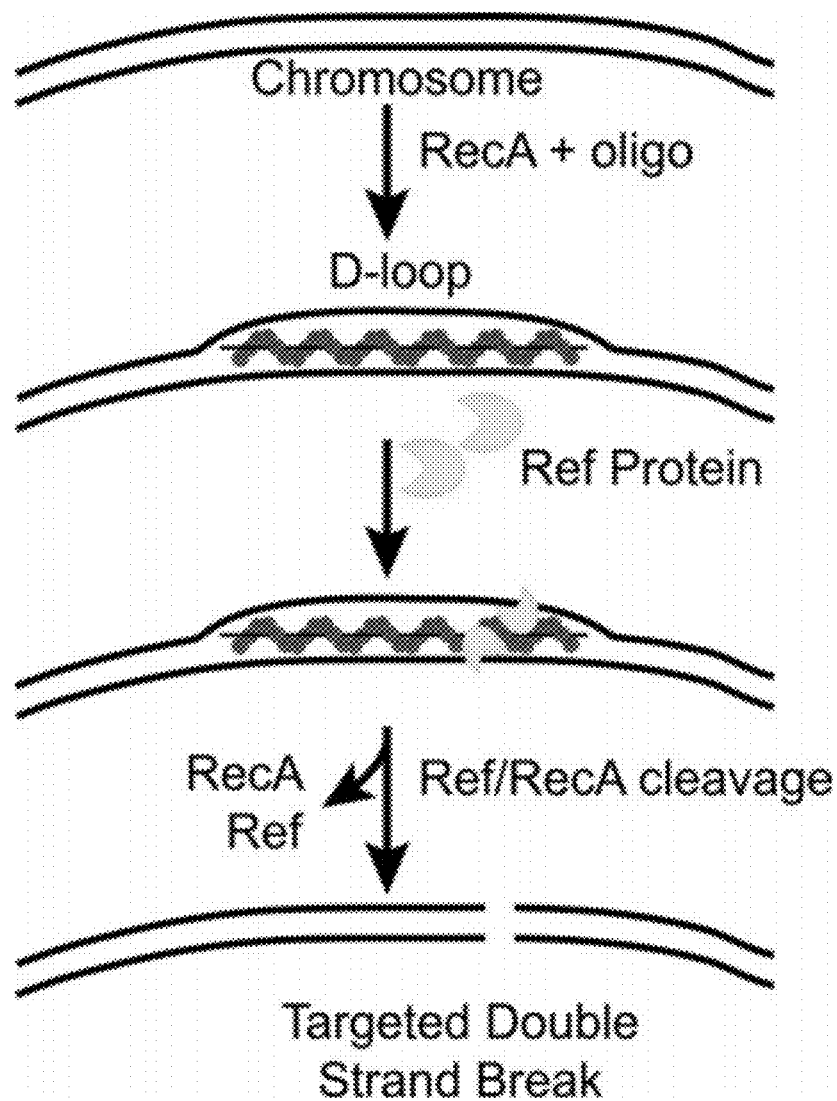
FIG. 16 is a diagram of a proposed scheme for the targeted cleavage of duplex DNA within RecA-mediated D-loops by the Ref protein of bacteriophage P1.

Ref will cleave RecA-bound ssDNA as well as DNA to which RecA nucleoprotein filaments are paired. When RecA filaments are restricted to oligonucleotides and used to form D-loops, the Ref/RecA system becomes a uniquely programmable nuclease system. Ref cleaves both strands of the targeted duplex DNA within the D-loop (FIGS. 14 and 15), introducing a double-strand break within a small target area. Cleavage can, thus, be introduced in an oligonucleotide-directed fashion. Used this way, Ref/RecA may be considered a universal restriction enzyme. The targeting reaction is illustrated in FIG. 16.

Cleavage of RecA-created D-loops has previously been reported for the S1 and Bal-31 nucleases (Shigemori and Oishi, 2004), both normally specific for single-stranded DNA. The unwound DNA at the ends of D-loops offers a target for such nucleases. The effects of the Ref nuclease differ from this earlier report in several important ways. First, neither S1 nor Bal-31 has any RecA-dependent phenotype in vivo. Second, both S1 and Bal31 will cleave single stranded DNA wherever it occurs, including at nicks and small gaps; Ref will cleave only where RecA protein is bound. It is likely that Ref evolved to work with RecA filaments. There is no such indication for the S1 and Bal-31 nucleases. Finally, the more proficient of the two nucleases, S1, requires a non-physiological set of reaction conditions to carry out its reaction efficiently.

The efficiency of oligonucleotide-directed Ref cleavage of DNA appears to be strongly dependent on the efficiency of RecA-mediated D-loop formation. This efficiency in turn can be modulated by the length of the DNA oligonucleotide, RecA mutant proteins with enhanced DNA binding and/or DNA pairing properties (the RecA E38K mutant protein is the most effective variant we have tested to date) and likely other factors that remain to be elucidated. Efficient targeted cleavage by the Ref/RecA system will provide a convenient and inexpensive method to introduce targeted double-strand breaks in a range of biotechnology applications.

Example 2

Improved Sequence-Targeted Endonuclease System (Prophetic)

The efficiency of the disclosed method is limited by the equilibrium dissociation (and rebinding) of the single-stranded DNA targeting fragment from the nucleoprotein filament of the RecA protein. In this prophetic example, we propose stabilizing the nucleoprotein filament to improve the efficiency of the nuclease activity of the disclosed system. The targeting DNA strand may be covalently linked, at its 5' end, to an engineered variant of RecA protein that includes six RecA subunits covalently linked together so as to form a permanent nucleation site. The covalently-linked RecA hexamer will effectively stabilize the nucleoprotein filament, and will provide a more efficient targeted endonuclease when contacted with Ref All publications, patents, and nucleotide and peptide sequences mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

The present invention is not intended to be limited to the foregoing examples, but encompasses all such modifications and variations as come within the scope of the appended claims.

REFERENCES

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., Mc-Coy, A. J., Moriarty, N. W., Oeffner, R., Read, R. J., Richardson, D. C., Richardson, J. S., Terwilliger, T. C., Zwart, P. H. (2010) *Acta Crystallogr. D Biol. Crystallogr.* 66, 213-221.

Brenner, S. L., Mitchell, R. S., Morrical, S. W., Neuendorf, S. K., Schutte, B. C., Cox, M. M. (1987) *J. Biol. Chem.* 262, 4011-4016.

Chen, Z., Yang, H., Pavletich, N. P. (2008) *Nature* 453, 489-494.

Cox, M. M. (2003) *Annu. Rev. Microbiol.* 57, 551-577.

Cox, M. M. (2007) *Crit. Rev. Biochem. Mol. Biol.* 42, 41-63.

Craig, N. L., J. W. Roberts (1981) *J. Biol. Chem.* 256, 8039-8044.

Emsley, P., Cowtan, K. (2004) *Acta Crystallogr. D Biol. Crystallogr.* 60, 2126-2132.

Garinot-Schneider, C., A. J. Pommer, G. R. Moore, C. Kleanthous, R. James (1996) *J. Mol. Biol.* 260, 731-742.

Geiselmann, J., Wang, Y., Seifried, S. E., and von Hippel, P. H. (1993) *Proc. Natl. Acad. Sci. U.S.A.* 90, 7754-7758.

Gruenig M. C., N. Renzette, E. Long, S. Chiteni-Pattu, R. B. Inman, M. M. Cox, S. J. Sandler (2008) *Mol. Microbiol.* 69, 1165-1179.

Jiang, Q., K. Karata, R. Woodgate, M. M. Cox, M. F. Goodman (2009) *Nature* 460, 359-363.

Harmon, F. G., Rehrauer, W. M., Kowalczykowski, S. C. (1996) *J. Biol. Chem.* 271, 23874-23883.

Haruta, N., X. N. Yu, S. X. Yang, E. H. Egelman, M. M. Cox (2003) *J. Biol. Chem.* 278, 52710-52723.

Hunt, J. B., S. H. Neece, H. K. Schachman, A. Ginsburg (1984) *J. Biol. Chem.* 259, 14793-14803.

Koch, W. H., D. G. Ennis, A. S. Levine, R. Woodgate (1992) *Mol. Gen. Genet.* 233, 443-448.

Laufer C. S., J. B. Hays, B. E. Windle, T. S. Schaefer, E. H. Lee, S. L. Hays, M. R. McClure (1989) *Genetics* 123, 465-476.

Le Provost F., S. Lillico, B. Passet, R. Young, B. Whitelaw, J. Vilotte (2010) *Trends Biotech* 28, 134-141.

Lohman, T. M., L. B. Overman, *J Biol Chem* 260, 3594 (1985).

Lusetti, S. L., O. N. Voloshin, R. B. Inman, R. D. Camerini-Otero, M. M. Cox (2004) *J. Biol. Chem.* 279, 30037-30046.

Lu, S. D., D. Lu, M. Gottesman (1989) *J. Bacteriol.* 171, 3427-3432.

Lusetti, S. L. and M. M. Cox (2002) *Ann. Rev. Biochem.* 71, 71-100.

Marrione, P. E., M. M. Cox (1995) *Biochemistry* 34, 9809-9818.

Mate, M. J. and C. Kleanthous (2004) *J. Biol. Chem.* 279, 34763-34769.

McIlwraith, M. J., and West, S. C. (2001) *J. Mol. Biol.* 305, 23-31.

Mehta P., K. Katta, S. Krishnaswamy (2004) *Protein Sci.* 13, 295-300.

Messing, J. (1983) *Methods Enzymol.* 101, 20-78.

Neuendorf, S. K., M. M. Cox (1986) *J. Biol. Chem.* 261, 8276-8282.

Otwinowski, Z., and W. Minor (1997) *Methods Enzymol.* 276, 307-326

Petrova, V., S. Chitteni-Pattu, J. C. Drees, R. B. Inman, M. M. Cox (2009) *Mol. Cell.* 36, 121-130.

Robu, M. E., R. B. Inman, M. M. Cox (2004) *J. Biol. Chem.* 279, 10973-10981.

Scott, C. T. (2005) *Nature Biotechnology* 23 (8), 915-918.

Shigemori, Y., and Oishi, M. (2004) *Nucleic Acids Res.* 32, e4.

Slilaty, S, N., J. W. Little (1987) *Proc. Natl. Acad. Sci. U.S.A.* 84, 3987-3991.

Stoddard, B. L. (2005) *Q. Rev. Biophys.* 38, 49-95.

Windle, B. E. and J. B. Hays (1986) *Proc. Natl. Acad. Sci. U.S.A.* 83, 3885-3889.

VanLoock M. S., X. Yu, S. Yang, V. E. Galkin, H. Huang, S. S. Rajan, W. F. Anderson, E. A.

Stohl, H. S. Seifert, E. H. Egelman (2003) *J. Mol. Biol.* 333, 345-354.

Winn, M. D., Isupov, M. N., Murshudov, G. N. (2001) *Acta Crystallogr. D Biol. Crystallogr.* 57, 122-133.

Yu, X. and E. H. Egelman, *J. Mol. Biol.* (1992) 227, 334-346.

---

We claim:

1. A method of cleaving a duplex DNA molecule at any target defined nucleotide sequence, comprising the steps of:

(a) assembling a complex of a single-stranded DNA targeting fragment comprising a nucleotide sequence homologous to a target nucleotide sequence of a duplex DNA molecule with a RecA protein comprising: (i) the amino acid sequence of SEQ ID NO:1; (ii) the amino acid sequence of SEQ ID NO:1 wherein lysine is substituted for glutamic acid at amino acid residue 38, or (iii) an amino acid sequence that has at least 90% sequence identity to SEQ ID NO:1, wherein the RecA functionality is retained;

(b) contacting the complex that is assembled in step (a) with the duplex DNA molecule; and (c) contacting a Ref protein comprising: (i) SEQ ID NO:2, or (ii) an amino acid sequence that has at least 90% sequence identity to SEQ ID NO:2, wherein the Ref functionality is retained with the duplex DNA molecule; wherein both strands of the targeted duplex DNA molecule are cleaved within the sequences defined by homology to the single-stranded DNA used as the targeting fragment.

2. The method of claim 1, wherein the RecA protein used in step 1(a) is a RecA protein comprising the amino acid sequence of SEQ ID NO:1 or a RecA protein comprising the amino acid sequence of SEQ ID NO:1 wherein lysine is substituted for glutamic acid at amino acid residue 38.

3. The method of claim 1, wherein the Ref protein used in step 1(c) is a Ref protein comprising the amino acid sequence of SEQ ID NO:2.

4. The method of claim 1, wherein the Ref protein comprising an amino acid sequence that has at least 90% sequence identity to SEQ ID NO:2 that is used in step 1(c) comprises a ββα-metal core fold motif having the amino acid sequence of amino acid residues 112-123 of SEQ ID NO:2, and further comprises two metal binding motifs, one such motif C-terminal to the ββα-metal core fold motif and comprising the amino acid sequence of amino acid residues 96-99 of SEQ ID NO:2, and one such motif N-terminal to the ββα-metal core fold motif and comprising the amino acid sequence of amino acid residues 130-133 of SEQ ID NO:2.

5. The method of claim 1, wherein the single-stranded DNA targeting fragment is from 30-1,000 nucleotides in length.

6. The method of claim 5, wherein the single-stranded DNA targeting fragment is from 90-1,000 nucleotides in length.

7. The method of claim 5, wherein the nucleotide sequence on the single-stranded DNA targeting fragment that is homologous to the target nucleotide sequence is from 60-150 nucleotides in length.

8. The method of claim 1, wherein one or more of steps 1(a), 1(b), and 1(c) occur within a solution comprising a divalent metal ion.

9. The method of claim 8, wherein the divalent metal ion is $Mg^{2+}$ or $Mn^{2+}$.

10. The method of claim 9, wherein the divalent metal ion is $Mg^{2+}$.

* * * * *

UNITED STATES PATENT AND TRADEMARK OFFICE
CERTIFICATE OF CORRECTION

PATENT NO. : 8,785,157 B2
APPLICATION NO. : 13/208985
DATED : July 22, 2014
INVENTOR(S) : Michael M. Cox, Marielle C. Eichhern-Gruenig and James L. Keck Page 1 of 1

It is certified that error appears in the above-identified patent and that said Letters Patent is hereby corrected as shown below:

In the Specification

Column 16, line 62 - "µmol" should be "pmol"

Signed and Sealed this
Sixteenth Day of December, 2014

Michelle K. Lee
*Deputy Director of the United States Patent and Trademark Office*

SEQUENCE LISTING

```
<160> NUMBER OF SEQ ID NOS: 23

<210> SEQ ID NO 1
<211> LENGTH: 353
<212> TYPE: PRT
<213> ORGANISM: Escherichia coli

<400> SEQUENCE: 1

Met Ala Ile Asp Glu Asn Lys Gln Lys Ala Leu Ala Ala Leu Gly
1               5                   10                  15

Gln Ile Glu Lys Gln Phe Gly Lys Gly Ser Ile Met Arg Leu Gly Glu
            20                  25                  30

Asp Arg Ser Met Asp Val Glu Thr Ile Ser Thr Gly Ser Leu Ser Leu
        35                  40                  45

Asp Ile Ala Leu Gly Ala Gly Gly Leu Pro Met Gly Arg Ile Val Glu
    50                  55                  60

Ile Tyr Gly Pro Glu Ser Ser Gly Lys Thr Thr Leu Thr Leu Gln Val
65                  70                  75                  80

Ile Ala Ala Ala Gln Arg Glu Gly Lys Thr Cys Ala Phe Ile Asp Ala
                85                  90                  95

Glu His Ala Leu Asp Pro Ile Tyr Ala Arg Lys Leu Gly Val Asp Ile
            100                 105                 110

Asp Asn Leu Leu Cys Ser Gln Pro Asp Thr Gly Glu Gln Ala Leu Glu
```

```
                115                 120                 125
Ile Cys Asp Ala Leu Ala Arg Ser Gly Ala Val Asp Ile Val Val
            130                 135                 140
Asp Ser Val Ala Ala Leu Thr Pro Lys Ala Glu Ile Glu Gly Glu Ile
145                 150                 155                 160
Gly Asp Ser His Met Gly Leu Ala Ala Arg Met Met Ser Gln Ala Met
                165                 170                 175
Arg Lys Leu Ala Gly Asn Leu Lys Gln Ser Asn Thr Leu Leu Ile Phe
            180                 185                 190
Ile Asn Gln Ile Arg Met Lys Ile Gly Val Met Phe Gly Asn Pro Glu
            195                 200                 205
Thr Thr Thr Gly Gly Asn Ala Leu Lys Phe Tyr Ala Ser Val Arg Leu
        210                 215                 220
Asp Ile Arg Arg Ile Gly Ala Val Lys Glu Gly Glu Asn Val Val Gly
225                 230                 235                 240
Ser Glu Thr Arg Val Lys Val Val Lys Asn Lys Ile Ala Ala Pro Phe
                245                 250                 255
Lys Gln Ala Glu Phe Gln Ile Leu Tyr Gly Glu Gly Ile Asn Phe Tyr
            260                 265                 270
Gly Glu Leu Val Asp Leu Gly Val Lys Glu Lys Leu Ile Glu Lys Ala
            275                 280                 285
Gly Ala Trp Tyr Ser Tyr Lys Gly Glu Lys Ile Gly Gln Gly Lys Ala
        290                 295                 300
Asn Ala Thr Ala Trp Leu Lys Asp Asn Pro Glu Thr Ala Lys Glu Ile
305                 310                 315                 320
Glu Lys Lys Val Arg Glu Leu Leu Leu Ser Asn Pro Asn Ser Thr Pro
                325                 330                 335
Asp Phe Ser Val Asp Asp Ser Glu Gly Val Ala Glu Thr Asn Glu Asp
            340                 345                 350
Phe

<210> SEQ ID NO 2
<211> LENGTH: 186
<212> TYPE: PRT
<213> ORGANISM: Bacteriophage P1

<400> SEQUENCE: 2

Met Lys Thr Ile Glu Gln Lys Ile Glu Gln Cys Arg Lys Trp Gln Lys
1               5                   10                  15
Ala Ala Arg Glu Arg Ala Ile Ala Arg Gln Arg Glu Lys Leu Ala Asp
            20                  25                  30
Pro Val Trp Arg Glu Ser Gln Tyr Gln Lys Met Arg Asp Thr Leu Asp
        35                  40                  45
Arg Arg Ile Ala Lys Gln Lys Glu Arg Pro Pro Ala Ser Lys Thr Arg
    50                  55                  60
Lys Ser Ala Val Lys Ile Lys Ser Arg Gly Leu Lys Gly Arg Thr Pro
65                  70                  75                  80
Thr Ala Glu Glu Arg Arg Ile Ala Asn Ala Leu Gly Ala Leu Pro Cys
                85                  90                  95
Ile Ala Cys Tyr Met His Gly Val Ile Ser Asn Glu Val Ser Leu His
            100                 105                 110
His Ile Ala Gly Arg Thr Ala Pro Gly Cys His Lys Lys Gln Leu Pro
        115                 120                 125
Leu Cys Arg Trp His His Gln His Ala Ala Pro Ala Glu Val Arg Glu
```

```
                    130                 135                 140
Lys Tyr Pro Trp Leu Val Pro Val His Ala Asp Gly Val Val Gly Gly
145                 150                 155                 160

Lys Lys Glu Phe Thr Leu Leu Asn Lys Ser Glu Met Glu Leu Leu Ala
                165                 170                 175

Asp Ala Tyr Glu Met Ala Asn Ile Met His
            180                 185

<210> SEQ ID NO 3
<211> LENGTH: 186
<212> TYPE: PRT
<213> ORGANISM: Bacteriophage phi-W39

<400> SEQUENCE: 3

Met Lys Thr Ile Glu Gln Lys Leu Glu Gln Arg Arg Glu Trp Gln Lys
1               5                   10                  15

Ala Ala Arg Glu Arg Ala Ile Ala Arg Gln Arg Glu Lys Leu Ala Asp
                20                  25                  30

Pro Ala Trp Arg Glu Ser Gln Tyr Gln Lys Met Arg Asp Ser Ile Asp
            35                  40                  45

Arg Arg Ile Ala Lys Gln Lys Glu Arg Pro Ala Ser Lys Thr Arg
 50                  55                  60

Lys Ser Ala Val Lys Ile Lys Ser Arg Gly Leu Lys Gly Arg Thr Pro
65                  70                  75                  80

Thr Ala Glu Glu Arg Thr Ile Ala Asn Ala Leu Gly Thr Leu Pro Cys
                85                  90                  95

Ile Ala Cys Tyr Met His Gly Val Ile Ser Glu Glu Val Ser Leu His
            100                 105                 110

His Ile Ser Gly Arg Thr Ala Pro Gly Cys His Lys Lys Gln Leu Pro
        115                 120                 125

Leu Cys Arg Trp His His Gln His Ala Ala Pro Ala Glu Val Arg Glu
130                 135                 140

Lys Tyr Pro Trp Leu Val Pro Val His Ala Asp Gly Val Val Gly Gly
145                 150                 155                 160

Lys Lys Glu Phe Thr Leu Leu Asn Lys Ser Glu Met Glu Leu Leu Ala
                165                 170                 175

Asp Ala Tyr Glu Met Ala Asn Ile Met His
            180                 185

<210> SEQ ID NO 4
<211> LENGTH: 216
<212> TYPE: PRT
<213> ORGANISM: Bacteriophage P7

<400> SEQUENCE: 4

Met Lys Thr Ile Glu Gln Lys Ile Glu Gln Cys Arg Lys Trp Gln Lys
1               5                   10                  15

Ala Ala Arg Glu Arg Ala Ile Ala Arg Gln Arg Glu Lys Leu Ala Asp
                20                  25                  30

Pro Ala Trp Arg Glu Ser Gln Tyr Gln Lys Met Arg Asn Thr Ile Asp
            35                  40                  45

Arg Arg Ile Ala Lys Gln Lys Glu Arg Pro Ala Ser Lys Thr Arg
 50                  55                  60

Lys Ser Ala Val Lys Ile Lys Ser Arg Asp Leu Lys Gly Arg Thr Pro
65                  70                  75                  80

Thr Ala Glu Glu Arg Arg Ile Ala Asn Ala Leu Gly Ala Leu Pro Cys
```

```
                    85                  90                  95
Ile Ala Cys Tyr Met His Gly Val Ile Ser Glu Glu Val Ser Leu His
                100                 105                 110
His Ile Ser Gly Arg Thr Ala Pro Gly Cys His Lys Lys Gln Leu Pro
                115                 120                 125
Leu Cys Arg Trp His His Gln His Ala Ala Pro Ala Glu Val Arg Glu
            130                 135                 140
Lys Tyr Pro Trp Leu Val Pro Val His Ala Asp Gly Val Val Gly Gly
145                 150                 155                 160
Lys Lys Glu Phe Thr Leu Leu Asn Lys Ser Glu Met Glu Leu Leu Ala
                165                 170                 175
Asp Ala Tyr Glu Arg Gly Leu Thr Leu Ser Gly Thr Lys Thr His Val
            180                 185                 190
Lys Gln Arg Phe Leu Pro Leu Thr Pro Leu Leu Met Val Ser Asp Val
        195                 200                 205
Leu Trp Ser Pro Val Leu Pro Ala
        210                 215

<210> SEQ ID NO 5
<211> LENGTH: 183
<212> TYPE: PRT
<213> ORGANISM: Salmonella enterica

<400> SEQUENCE: 5

Met Ile Leu Thr Glu Gln Gln Ile Glu Arg Arg Gln Arg Ala Ile
1               5                   10                  15
Glu Ala Lys Asn Arg Ala Ile Ala Lys Gln Arg Ala Lys Met Ser Asp
                20                  25                  30
Pro Ala Trp Arg Ala Glu Gln Tyr Gln Lys Arg Arg Asp Ala Glu Asn
            35                  40                  45
Arg Arg Arg Glu Arg Met Arg Ser Ser Pro Pro Ala Lys Pro Arg
    50                  55                  60
Lys Pro Val Lys Ser Arg Gly Leu Lys Gly Arg Thr Pro Thr Ala Glu
65                  70                  75                  80
Glu Lys Arg Thr Ala Asn Ala Leu Gly Ser Leu Pro Cys Ile Ala Cys
                85                  90                  95
Tyr Ile His Gly Val Ile Asn His Val Val Ser Leu His His Ile Asp
                100                 105                 110
Gly Arg Thr Ala Pro Asp Cys His Lys Lys Gln Leu Pro Leu Cys Asn
            115                 120                 125
Trp His His Gln Tyr Ala Ala Pro Pro Glu Ile Arg Lys Ile Tyr Pro
        130                 135                 140
Trp Leu Val Pro Val His Ala Asp Gly Asn Val Gly Gly Lys Ser Glu
145                 150                 155                 160
Phe Ser Arg Leu Asn Lys Pro Glu Arg Glu Leu Leu Val Asp Ala Tyr
                165                 170                 175
Ala Leu Ala Gly Leu Leu Val
            180

<210> SEQ ID NO 6
<211> LENGTH: 120
<212> TYPE: PRT
<213> ORGANISM: Bordetella avium

<400> SEQUENCE: 6

Met Lys Gly Arg Asn Pro Thr Ala Glu Gln Lys Arg Phe Trp Asp Met
```

```
1               5                   10                  15
Leu Ala Arg Asn Ile Gly Cys Val Ala Ser Arg Met Asp Gly Phe Phe
                20                  25                  30
Asp Ser Gln Cys Leu Ile His His Ile Asp Gly Arg Thr Lys Pro Asp
                35                  40                  45
Ala His Trp Leu Val Leu Pro Leu Ser Ala Gly Asn His Gln Asp Gly
        50                  55                  60
Thr Gly Ala Pro Gly Arg Ile Ala Val His Pro Trp Lys Thr Arg Phe
65                  70                  75                  80
Glu Glu Arg Tyr Gly Lys Gln Arg Asp Leu Leu Val Trp Cys Ile Glu
                    85                  90                  95
Gln Leu Gln Ala Gln Gly Leu Asn Val Pro Asp Gly Ala Leu Arg Ala
                100                 105                 110
Ala Gly Met Leu Glu Glu Ser Arg
        115                 120
```

<210> SEQ ID NO 7
<211> LENGTH: 150
<212> TYPE: DNA
<213> ORGANISM: Artificial Sequence
<220> FEATURE:
<223> OTHER INFORMATION: Synthetic polynucleotide

<400> SEQUENCE: 7
ttttggtttt tatcgtcgtc tggtaaacga gggttatgat agtgttgctc ttactatgcc      60
tcgtaattcc ttttggcgtt atgtatctgc attagttgaa tgtggtattc ctaaatctca     120
actgatgaat ctttctacct gtaataatgt                                      150

<210> SEQ ID NO 8
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 8
attcttacgc tttcaggtca gaagggttct atctctgttg gccagaatgt cccttttatt      60

<210> SEQ ID NO 9
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 9
ggcctcgcgg tagctgagct cggagcgcac gattcgcact gctgatgttc                 50

<210> SEQ ID NO 10
<211> LENGTH: 149
<212> TYPE: DNA
<213> ORGANISM: Artificial Sequence
<220> FEATURE:
<223> OTHER INFORMATION: Synthetic polynucleotide

<400> SEQUENCE: 10
gcatttggct accctgccac tcacaccatt caggcgcctg gccgcgtgaa tttgattggt      60
gaacacaccg actacaacga cggtttcgtt ctgccctgcg cgattgatta tcaaaccgtg     120
atcagttgtg caccacgcga tgaccgtaa                                       149

<210> SEQ ID NO 11
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 11
taacatcagc agtgcgaatc gtgcgctccg agctcagcta ccgcgaggcc tgca       54

<210> SEQ ID NO 12
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 12
gaacatcagc agtgcgaatc gtgcgctccg agctcagcta ccgcgaggcc             50

<210> SEQ ID NO 13
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 13
gaacatcagc agtgcgaatc gtgcgctccg agctcagcta ccgcgaggcc tgca       54

<210> SEQ ID NO 14
<211> LENGTH: 150
<212> TYPE: DNA
<213> ORGANISM: Artificial Sequence
<220> FEATURE:
<223> OTHER INFORMATION: Synthetic polynucleotide

<400> SEQUENCE: 14
tcccgactgg aaagcgggca gtgagcgcaa cgcaattaat gtgagttagc tcactcatta      60
ggcaccccag gctttacact ttatgcttcc ggctcgtatg ttgtgtggaa ttgtgagcgg     120
ataacaattt cacacaggaa acagctatga                                     150

<210> SEQ ID NO 15
<211> LENGTH: 41
<212> TYPE: DNA
<213> ORGANISM: Artificial Sequence
<220> FEATURE:
<223> OTHER INFORMATION: Synthetic oligonucleotide for Holliday junction
      formation.

<400> SEQUENCE: 15
cccgtgatca ccaatgcaga ttgacgaacc tttgcccacg t                     41

<210> SEQ ID NO 16
<211> LENGTH: 41
<212> TYPE: DNA
<213> ORGANISM: Artificial Sequence
<220> FEATURE:
<223> OTHER INFORMATION: Synthetic oligonucleotide for Holliday junction
      formation.

<400> SEQUENCE: 16
gacgtgggca aaggttcgtc aatggactga cagctgcatg g                     41

```
<210> SEQ ID NO 17
<211> LENGTH: 41
<212> TYPE: DNA
<213> ORGANISM: Artificial Sequence
<220> FEATURE:
<223> OTHER INFORMATION: Synthetic oligonucleotide for Holliday junction
      formation.

<400> SEQUENCE: 17
gccatgcagc tgtcagtcca ttgtcatgct aggcctactg c                    41

<210> SEQ ID NO 18
<211> LENGTH: 41
<212> TYPE: DNA
<213> ORGANISM: Artificial Sequence
<220> FEATURE:
<223> OTHER INFORMATION: Synthetic oligonucleotide for Holliday junction
      formation.

<400> SEQUENCE: 18
ggcagtaggc ctagcatgac aatctgcatt ggtgatcacg g                    41

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide for the formation of
      branched annealed structures.

<400> SEQUENCE: 19
gacgtgggca aaggttcgt                                             19

<210> SEQ ID NO 20
<211> LENGTH: 18
<212> TYPE: DNA
<213> ORGANISM: Artificial Sequence
<220> FEATURE:
<223> OTHER INFORMATION: Synthetic oligonucleotide for forming branched
      annealed structures.

<400> SEQUENCE: 20
tcatgctagg cctactgc                                              18

<210> SEQ ID NO 21
<211> LENGTH: 363
<212> TYPE: PRT
<213> ORGANISM: Deinococcus radiodurans

<400> SEQUENCE: 21

Met Ser Lys Asp Ala Thr Lys Glu Ile Ser Ala Pro Thr Asp Ala Lys
1               5                   10                  15

Glu Arg Ser Lys Ala Ile Glu Thr Ala Met Ser Gln Ile Glu Lys Ala
            20                  25                  30

Phe Gly Lys Gly Ser Ile Met Lys Leu Gly Ala Glu Ser Lys Leu Asp
        35                  40                  45

Val Gln Val Val Ser Thr Gly Ser Leu Ser Leu Asp Leu Ala Leu Gly
    50                  55                  60

Val Gly Gly Ile Pro Arg Gly Arg Ile Thr Glu Ile Tyr Gly Pro Glu
65                  70                  75                  80

Ser Gly Gly Lys Thr Thr Leu Ala Leu Ala Ile Val Ala Gln Ala Gln
                85                  90                  95

Lys Ala Gly Gly Thr Cys Ala Phe Ile Asp Ala Glu His Ala Leu Asp
            100                 105                 110
```

```
Pro Val Tyr Ala Arg Ala Leu Gly Val Asn Thr Asp Glu Leu Leu Val
            115                 120                 125

Ser Gln Pro Asp Asn Gly Glu Gln Ala Leu Glu Ile Met Glu Leu Leu
    130                 135                 140

Val Arg Ser Gly Ala Ile Asp Val Val Val Asp Ser Val Ala Ala
145                 150                 155                 160

Leu Thr Pro Arg Ala Glu Ile Glu Gly Asp Met Gly Asp Ser Leu Pro
                165                 170                 175

Gly Leu Gln Ala Arg Leu Met Ser Gln Ala Leu Arg Lys Leu Thr Ala
                180                 185                 190

Ile Leu Ser Lys Thr Gly Thr Ala Ala Ile Phe Ile Asn Gln Val Arg
            195                 200                 205

Glu Lys Ile Gly Val Met Tyr Gly Asn Pro Glu Thr Thr Thr Gly Gly
        210                 215                 220

Arg Ala Leu Lys Phe Tyr Ala Ser Val Arg Leu Asp Val Arg Lys Ile
225                 230                 235                 240

Gly Gln Pro Thr Lys Val Gly Asn Asp Ala Val Ala Asn Thr Val Lys
                245                 250                 255

Ile Lys Thr Val Lys Asn Lys Val Ala Ala Pro Phe Lys Glu Val Glu
            260                 265                 270

Leu Ala Leu Val Tyr Gly Lys Gly Phe Asp Gln Leu Ser Asp Leu Val
        275                 280                 285

Gly Leu Ala Ala Asp Met Asp Ile Ile Lys Lys Ala Gly Ser Phe Tyr
        290                 295                 300

Ser Tyr Gly Asp Glu Arg Ile Gly Gln Gly Lys Glu Lys Thr Ile Ala
305                 310                 315                 320

Tyr Ile Ala Glu Arg Pro Glu Met Glu Gln Glu Ile Arg Asp Arg Val
                325                 330                 335

Met Ala Ala Ile Arg Ala Gly Asn Ala Gly Glu Ala Pro Ala Leu Ala
                340                 345                 350

Pro Ala Pro Ala Ala Pro Glu Ala Ala Glu Ala
            355                 360
```

<210> SEQ ID NO 22
<211> LENGTH: 186
<212> TYPE: PRT
<213> ORGANISM: Pseudomonas aeruginosa

<400> SEQUENCE: 22

```
Glu Arg Gln Phe Gly Lys Gly Ala Val Met Arg Met Gly Asp His Glu
1               5                   10                  15

Arg Gln Ala Ile Pro Ala Ile Ser Thr Gly Ser Leu Gly Leu Asp Ile
            20                  25                  30

Ala Leu Gly Ile Gly Gly Leu Pro Lys Gly Arg Ile Val Glu Ile Tyr
        35                  40                  45

Gly Pro Glu Ser Ser Gly Lys Thr Thr Leu Thr Leu Ser Val Ile Ala
    50                  55                  60

Glu Ala Gln Lys Gln Gly Ala Thr Cys Ala Phe Val Asp Ala Glu His
65                  70                  75                  80

Ala Leu Asp Pro Asp Tyr Ala Gly Lys Leu Gly Val Asn Val Asp Asp
                85                  90                  95

Leu Leu Val Ser Gln Pro Asp Thr Gly Glu Gln Ala Leu Glu Ile Thr
            100                 105                 110

Asp Met Leu Val Arg Ser Asn Ala Val Asp Val Ile Ile Val Asp Ser
```

```
            115                 120                 125
Val Ala Ala Leu Val Pro Lys Ala Glu Ile Glu Gly Glu Met Gly Asp
        130                 135                 140
Ala His Val Gly Leu Gln Ala Arg Leu Met Ser Gln Ala Leu Arg Lys
145                 150                 155                 160
Ile Thr Gly Asn Ile Lys Asn Ala Asn Cys Leu Val Ile Phe Ile Asn
                165                 170                 175
Gln Ile Arg Met Lys Ile Gly Val Met Phe
                180                 185

<210> SEQ ID NO 23
<211> LENGTH: 274
<212> TYPE: PRT
<213> ORGANISM: Neisseria gonorrhoeae

<400> SEQUENCE: 23

Ala Ile Met Lys Met Asp Gly Ser Gln Gln Glu Glu Asn Leu Glu Val
1               5                   10                  15
Ile Ser Thr Gly Ser Leu Gly Leu Asp Leu Ala Leu Gly Val Gly Gly
                20                  25                  30
Leu Pro Arg Gly Arg Ile Val Glu Ile Phe Gly Pro Glu Ser Ser Gly
            35                  40                  45
Lys Thr Thr Leu Cys Leu Glu Ala Val Ala Gln Cys Gln Lys Asn Gly
    50                  55                  60
Gly Val Cys Ala Phe Val Asp Ala Glu His Ala Phe Asp Pro Val Tyr
65                  70                  75                  80
Ala Arg Lys Leu Gly Val Lys Val Glu Leu Tyr Leu Ser Gln Pro
                85                  90                  95
Asp Thr Gly Glu Gln Ala Leu Glu Ile Cys Asp Thr Leu Val Arg Ser
                100                 105                 110
Gly Gly Ile Asp Met Val Val Val Asp Ser Val Ala Ala Leu Val Pro
            115                 120                 125
Lys Ala Glu Ile Glu Gly Asp Met Gly Asp Ser His Val Gly Leu Gln
    130                 135                 140
Ala Arg Leu Met Ser Gln Ala Leu Arg Lys Leu Thr Gly His Ile Lys
145                 150                 155                 160
Lys Thr Asn Thr Leu Val Val Phe Ile Asn Gln Ile Arg Met Lys Ile
                165                 170                 175
Gly Val Met Phe Gly Ser Pro Glu Thr Thr Thr Gly Gly Asn Ala Leu
                180                 185                 190
Lys Phe Tyr Ser Ser Val Arg Leu Asp Ile Arg Arg Thr Gly Ser Ile
            195                 200                 205
Lys Lys Gly Glu Glu Val Leu Gly Asn Glu Thr Arg Val Lys Val Ile
    210                 215                 220
Lys Asn Lys Val Ala Pro Pro Phe Arg Gln Ala Glu Phe Asp Ile Leu
225                 230                 235                 240
Tyr Gly Glu Gly Ile Ser Trp Glu Gly Glu Leu Ile Asp Ile Gly Val
                245                 250                 255
Lys Asn Asp Ile Ile Asn Lys Ser Gly Ala Trp Tyr Ser Tyr Asn Gly
                260                 265                 270
Ala Lys
```